US009980779B2

(12) United States Patent
Hurley et al.

(10) Patent No.: US 9,980,779 B2
(45) Date of Patent: May 29, 2018

(54) METHOD AND SYSTEM FOR ASSEMBLY OF A MODULAR PROSTHETIC SOCKET BASED ON RESIDUAL LIMB METRICS

(71) Applicant: LIM INNOVATIONS, INC., San Francisco, CA (US)

(72) Inventors: Garrett Ray Hurley, San Francisco, CA (US); Andrew C. Pedtke, San Francisco, CA (US)

(73) Assignee: LIM Innovations, Inc., San Francisco, CA (US)

( * ) Notice: Subject to any disclaimer, the term of this patent is extended or adjusted under 35 U.S.C. 154(b) by 719 days.

(21) Appl. No.: 14/572,571

(22) Filed: Dec. 16, 2014

(65) Prior Publication Data
US 2015/0168943 A1    Jun. 18, 2015

Related U.S. Application Data

(60) Provisional application No. 62/045,433, filed on Sep. 3, 2014, provisional application No. 62/007,742, filed
(Continued)

(51) Int. Cl.
*G06F 7/00* (2006.01)
*A61B 19/00* (2006.01)
(Continued)

(52) U.S. Cl.
CPC ............ *A61B 19/50* (2013.01); *A61F 2/5046* (2013.01); *A61F 2/76* (2013.01); *A61F 2/80* (2013.01);
(Continued)

(58) Field of Classification Search
None
See application file for complete search history.

(56) References Cited

U.S. PATENT DOCUMENTS 1,144,681 A    6/1915 Apgar
1,893,853 A    1/1933 Tullis
(Continued)

FOREIGN PATENT DOCUMENTS

DE    319623    3/1920
EP    0204407 A2    12/1986
(Continued)

OTHER PUBLICATIONS

Quigley, Michael. Prosthetic Management: Overview, Methods and Materials. Chapter 4. Atlas of Limb Prosthetics: Surgical, Prosthetic, and Rehabilitation Principles. (Second Edition) 1992.
(Continued)

*Primary Examiner* — Yolanda R Cumbess
(74) *Attorney, Agent, or Firm* — Gordon & Jacobson, P.C.

(57) ABSTRACT

A method of providing a modular prosthetic socket for a residual limb of a patient may involve receiving digital data defining a three-dimensional digital profile of the residual limb and selecting prosthetic socket components from component-specific inventories, based at least in part on the digital profile. The selected prosthetic socket components may include: multiple longitudinal struts; one or more proximal brim members for attachment to the longitudinal struts; and a distal socket base to which the longitudinal struts attach at or near their distal ends. The method may further involve providing the selected prosthetic components to an operator for assembling into the modular prosthetic socket. The prosthetic socket, when assembled, defines an internal space substantially complementary to the profile of the residual limb.

42 Claims, 14 Drawing Sheets

Related U.S. Application Data on Jun. 4, 2014, provisional application No. 61/916,579, filed on Dec. 16, 2013.

(51) Int. Cl.
- *A61F 2/50* (2006.01)
- *A61F 2/76* (2006.01)
- *A61F 2/80* (2006.01)
- *A61F 2/78* (2006.01)

(52) U.S. Cl.
CPC .......... A61F 2002/5016 (2013.01); A61F 2002/5083 (2013.01); A61F 2002/7881 (2013.01); G05B 2219/31044 (2013.01); G05B 2219/45172 (2013.01)

(56) References Cited

U.S. PATENT DOCUMENTS

| | | |
|---|---|---|
| 2,025,835 A | 12/1935 | Trautman |
| 2,229,728 A | 1/1941 | Eddels |
| 2,634,424 A | 4/1953 | O'Gorman |
| 2,759,271 A | 8/1956 | Von Duyke |
| 2,908,016 A | 10/1959 | Botko |
| 2,949,674 A | 8/1960 | Wexler |
| 3,678,587 A | 7/1972 | Madden |
| 4,161,042 A | 7/1979 | Collingham et al. |
| 4,225,982 A | 10/1980 | Cochrane et al. |
| 4,300,245 A | 11/1981 | Saunders |
| 4,459,709 A | 7/1984 | Leal et al. |
| 4,704,129 A | 11/1987 | Massey |
| 4,715,124 A | 12/1987 | Harrington |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,988,360 A | 1/1991 | Shamp |
| 5,003,969 A | 4/1991 | Azer et al. |
| 5,014,441 A | 5/1991 | Pratt |
| 5,108,456 A | 4/1992 | Coonan, III |
| 5,116,382 A | 5/1992 | Steinkamp et al. |
| 5,133,777 A | 7/1992 | Arbogast et al. |
| 5,168,635 A | 12/1992 | Hoffman |
| 5,201,773 A | 4/1993 | Carideo, Jr. |
| 5,201,775 A | 4/1993 | Arbogast et al. |
| 5,246,464 A | 9/1993 | Sabolich |
| 5,312,669 A | 5/1994 | Bedard |
| 5,387,245 A | 2/1995 | Fay et al. |
| 5,431,624 A | 7/1995 | Saxton et al. |
| 5,503,543 A | 4/1996 | Laghi |
| 5,520,529 A | 5/1996 | Heckel |
| 5,529,575 A | 6/1996 | Klotz |
| 5,529,576 A | 6/1996 | Lundt et al. |
| 5,651,792 A | 7/1997 | Telikicherla |
| 5,652,053 A | 7/1997 | Liegeois |
| 5,718,925 A | 2/1998 | Kristinsson et al. |
| 5,728,165 A | 3/1998 | Brown, Sr. |
| 5,800,565 A | 9/1998 | Biedermann |
| 5,824,111 A | 10/1998 | Schall et al. |
| 5,885,509 A | 3/1999 | Kristinsson |
| 5,888,215 A | 3/1999 | Roos et al. |
| 5,888,217 A | 3/1999 | Siemker |
| 5,944,679 A | 8/1999 | DeToro |
| 6,033,440 A | 3/2000 | Schall et al. |
| 6,051,026 A | 4/2000 | Biedermann et al. |
| 6,206,932 B1 | 3/2001 | Johnson |
| 6,228,124 B1 | 5/2001 | Slemker et al. |
| 6,231,618 B1 | 5/2001 | Schall et al. |
| D453,591 S | 2/2002 | Garden |
| 6,368,357 B1 | 4/2002 | Schon et al. |
| 6,443,282 B1* | 9/2002 | Kwoka .............. B60K 17/351 192/48.4 |
| 6,444,282 B1 | 9/2002 | Shirer |
| 6,458,163 B1 | 10/2002 | Slemker et al. |
| 6,497,028 B1 | 12/2002 | Rothschild et al. |
| 6,500,210 B1 | 12/2002 | Sabolich et al. |
| 6,576,022 B2 | 6/2003 | Meyer et al. |
| 6,669,736 B2 | 12/2003 | Slemker et al. |
| 6,700,563 B1 | 3/2004 | Koizumi |
| 6,761,743 B1 | 7/2004 | Johnson |
| 6,767,332 B1 | 7/2004 | Pardue |
| 6,942,703 B2 | 9/2005 | Carstens |
| 6,974,484 B2 | 12/2005 | Caspers |
| 7,090,700 B2 | 8/2006 | Curtis |
| 7,105,122 B2 | 9/2006 | Karason |
| 7,172,714 B2 | 2/2007 | Jacobson |
| 7,240,414 B2 | 7/2007 | Taylor, Sr. |
| 7,300,466 B1 | 11/2007 | Martin |
| 7,318,504 B2 | 1/2008 | Vitale et al. |
| 7,338,532 B2 | 3/2008 | Haberman et al. |
| 7,344,567 B2 | 3/2008 | Slemker |
| 7,402,265 B2 | 7/2008 | Jacobson |
| 7,479,163 B2 | 1/2009 | Slemker et al. |
| 7,591,857 B2 | 9/2009 | Slemker et al. |
| 7,658,720 B2 | 2/2010 | Johnson |
| 7,753,866 B2 | 7/2010 | Jackovitch |
| 7,762,973 B2 | 7/2010 | Einarsson et al. |
| 7,980,921 B2 | 7/2011 | Saravanos |
| 7,985,192 B2 | 7/2011 | Sheehan et al. |
| 8,083,807 B2 | 12/2011 | Auberger et al. |
| 8,088,320 B1 | 1/2012 | Bedard |
| 8,116,900 B2 | 2/2012 | Slemker et al. |
| 8,142,517 B2 | 3/2012 | Horie |
| 8,303,527 B2 | 11/2012 | Joseph |
| 8,323,353 B1 | 12/2012 | Alley et al. |
| 8,382,852 B2 | 2/2013 | Laghi |
| 8,403,993 B2 | 3/2013 | Aram et al. |
| 8,465,445 B2 | 6/2013 | George |
| 8,470,050 B2 | 6/2013 | Dillingham |
| 8,535,389 B2 | 9/2013 | McKinney |
| 8,576,250 B2 | 11/2013 | Sabiston et al. |
| 8,894,719 B2 | 11/2014 | Egilsson et al. |
| D723,163 S | 2/2015 | Gottlieb |
| 8,978,224 B2 | 3/2015 | Hurley et al. |
| 9,044,349 B2 | 6/2015 | Hurley et al. |
| 9,155,636 B1 | 10/2015 | Fikes |
| 9,265,629 B2 | 2/2016 | Kelley et al. |
| 9,345,590 B2 | 5/2016 | Arabian et al. |
| 9,468,542 B2 | 10/2016 | Hurley et al. |
| 9,468,543 B2 | 10/2016 | Hurley et al. |
| 9,474,633 B2 | 10/2016 | Williams et al. |
| 9,549,828 B2 | 1/2017 | Hurley et al. |
| D778,452 S | 2/2017 | Cespedes et al. |
| 2002/0099450 A1 | 7/2002 | Dean et al. |
| 2003/0181990 A1 | 9/2003 | Phillips |
| 2004/0158332 A1 | 8/2004 | Carstens |
| 2004/0204771 A1 | 10/2004 | Swanson, Sr. |
| 2004/0260402 A1 | 12/2004 | Baldini et al. |
| 2006/0009860 A1 | 1/2006 | Price, Jr. |
| 2006/0020348 A1* | 1/2006 | Slemker .............. A61B 5/107 623/33 |
| 2006/0020349 A1 | 1/2006 | Slemker |
| 2007/0004993 A1 | 1/2007 | Coppens et al. |
| 2007/0078523 A1 | 4/2007 | Kholwadwala et al. |
| 2007/0152379 A1 | 7/2007 | Jacobson |
| 2007/0298075 A1 | 12/2007 | Borgia et al. |
| 2008/0269914 A1 | 10/2008 | Coppens et al. |
| 2009/0036999 A1 | 2/2009 | Egilsson et al. |
| 2009/0076625 A1 | 3/2009 | Groves et al. |
| 2009/0105844 A1 | 4/2009 | Ortiz |
| 2009/0240344 A1 | 9/2009 | Colvin et al. |
| 2009/0299490 A1 | 12/2009 | Summit |
| 2010/0016772 A1 | 1/2010 | DeToro et al. |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0160722 A1 | 6/2010 | Kuyava et al. |
| 2010/0274364 A1 | 10/2010 | Pacanowsky et al. |
| 2011/0029096 A1 | 2/2011 | Laghi |
| 2011/0071647 A1 | 3/2011 | Mahon |
| 2011/0114635 A1 | 5/2011 | Sheehan |
| 2011/0160871 A1 | 6/2011 | Boone et al. |
| 2011/0232837 A9 | 9/2011 | Ottleben |
| 2011/0320010 A1 | 12/2011 | Vo |

(56) References Cited

U.S. PATENT DOCUMENTS

| | | | |
|---|---|---|---|
| 2012/0022667 A1 | 1/2012 | Accinni et al. | |
| 2012/0041567 A1 | 2/2012 | Cornell | |
| 2012/0101417 A1 | 4/2012 | Joseph | |
| 2012/0101597 A1 | 4/2012 | Bache | |
| 2012/0143077 A1 | 6/2012 | Sanders et al. | |
| 2012/0165956 A1 | 6/2012 | Li | |
| 2012/0191218 A1 | 7/2012 | McCarthy | |
| 2012/0215324 A1 | 8/2012 | King | |
| 2012/0253475 A1 | 10/2012 | Kelley et al. | |
| 2012/0271210 A1 | 10/2012 | Galea et al. | |
| 2012/0271214 A1 | 10/2012 | Blanck | |
| 2012/0271433 A1 | 10/2012 | Galea et al. | |
| 2012/0293411 A1 | 11/2012 | Leithinger et al. | |
| 2013/0123940 A1 | 5/2013 | Hurley et al. | |
| 2013/0192071 A1 | 8/2013 | Esposito et al. | |
| 2013/0197318 A1 | 8/2013 | Herr et al. | |
| 2013/0245785 A1 | 9/2013 | Accini et al. | |
| 2013/0282141 A1 | 10/2013 | Herr et al. | |
| 2014/0005801 A1 | 1/2014 | Van der Watt et al. | |
| 2014/0031953 A1 | 1/2014 | MacKenzie | |
| 2014/0121783 A1 | 5/2014 | Alley | |
| 2014/0149082 A1 | 5/2014 | Sanders et al. | |
| 2014/0180185 A1 | 6/2014 | Zachariasen | |
| 2014/0277584 A1 | 9/2014 | Hurley et al. | |
| 2014/0277585 A1 | 9/2014 | Kelley et al. | |
| 2014/0379097 A1 | 12/2014 | Hurley et al. | |
| 2015/0168943 A1 | 6/2015 | Hurley et al. | |
| 2015/0190252 A1 | 7/2015 | Hurley et al. | |
| 2015/0265434 A1 | 9/2015 | Hurley et al. | |
| 2015/0352775 A1 | 12/2015 | Geshlider et al. | |
| 2016/0000587 A1 | 1/2016 | Hurley et al. | |
| 2016/0022466 A1 | 1/2016 | Pedtke et al. | |
| 2016/0058584 A1 | 3/2016 | Cespedes et al. | |
| 2016/0143752 A1 | 5/2016 | Hurley et al. | |
| 2016/0235560 A1 | 8/2016 | Cespedes et al. | |
| 2016/0334780 A1 | 11/2016 | Dair et al. | |
| 2017/0027718 A1 | 2/2017 | Williams et al. | |
| 2017/0027720 A1 | 2/2017 | Pedtke et al. | |
| 2017/0079811 A1 | 3/2017 | Kelley et al. | |

FOREIGN PATENT DOCUMENTS

| | | | | |
|---|---|---|---|---|
| EP | 1433447 A2 | 6/2004 | | |
| GB | 127451 A | 6/1919 | | |
| GB | 2080114 A | 2/1982 | | |
| GB | 2080114 A | * 2/1982 | ............... | A61F 2/60 |
| WO | 1991016019 | 10/1991 | | |
| WO | 1998012994 | 4/1998 | | |
| WO | 2000/003665 | 1/2000 | | |
| WO | 2000003665 A1 | 1/2000 | | |
| WO | 2000/030572 | 6/2000 | | |
| WO | 2007035875 | 3/2007 | | |
| WO | 2008116025 | 9/2008 | | |
| WO | 2009093020 | 7/2009 | | |
| WO | 2012021823 | 2/2012 | | |
| WO | 2014/004709 | 1/2014 | | |
| WO | 2014/068269 A1 | 5/2014 | | |

OTHER PUBLICATIONS

Koike, K. The TC double socket above-knee prosthesis. Prosthetic and Orthotics International. 1981, 5(3): 129-134.
Comfil (thermoformable composite technique). Fillauer Fabrication Manual. Jun. 15, 2012.
Fairley. From Academia to the Developing World. O&P Edge Magazine. May 2011.
Jana. Designing a cheaper, simpler prosthetic arm. ZDNet. Nov. 14, 2011.
Gleave. A plastic socket and stump casting technique for above-knee prostheses. Hong Kong Medical Department. vol. 47, No. 1, Feb. 1965.
Hwang. Winner-Spark! Spark Galleries. 2012.
Turner. Fit for Everyone. Yank Design. Jul. 17, 2013.
Wilson. Recent Advances in Above-Knee Prosthetics. Artificial Limbs. vol. 12, No. 2, 1968.
International Search Report dated Mar. 31, 2015, for application PCT/US2014/070666 filed Dec. 16, 2014.
Written Opinion dated Mar. 31, 2015, for application PCT/US2014/070666 filed Dec. 16, 2014.
Supplementary European Search Report and Opinion dated Jul. 21, 2015, for application EP 12847452.5 filed Nov. 13, 2012.
Hanger Inc., "ComfortFlex Socket System," downloaded from http://www.hanger.com/prosthetics/services/Technology/Pages/ComfortFlex.aspx, 2 pages, archived Sep. 17, 2012.
Instamorph, "Moldable Plastic: Instructions" downloaded from URL: <http://www.instamorph.com/instructions>, 2 pages, archived Dec. 24, 2011.
Ottobock, "PU Resin Kit Polytol®" downloaded from the internet: <URL: http://www.ottobock.com/cps.rde/xchg/ob_com_en/hs.xsl/17414.html> on Dec. 17, 2012, 2 pages.
Zhang, "Ethylene-vinyl acetate copolymer based on a continuous phase of dual/polycaprolactone blend of the porous material prepared," Yangzhou University, Materials Science, Master's Thesis, [USPTO translation of relevant portions of Zhang article], 131 pages, 2010.
Comfil (thermoformable composite technique). Fillauer Fabrication Manuel. Jun. 15, 2012.
Compton, Compton table. "New plastics for forming directly on the patient." Prosthetics and Orthotics International, 1978, vol. 2, No. 1, pp. 43-47.
Fairley, Miki. Socket can be fabricated, modified, fitted-in one hour. O&P Edge Magazine. Jun. 2007.
Allard. Cut-4-Custom: Custom TLSO in less than an hour. O&P Edge Magazine. Jul. 2010.
Instamorph. Remoldable prosthetics. Apr. 2013. <www.instamorph.com/ideas/outdoors-and-ergonomics/remoldable-prosthetics>.
Kelley et al. U.S. Appl. No. 61/794,948, filed Mar. 15, 2013.
Ottobock: PU Resin Kit Polytol; downloaded Dec. 17, 2012 from http://www.ottobock.com/cps.rde/xchg/ob_com_en/hs.xsl/17414.html. (2 pages).
Hanger ComfortFlex Socket System for Prosthetic Devices: website pages downloaded Nov. 28, 2012 from http://www.hanger.com/prosthetics/services/Technology/Pages/ComfortFlex.aspx. (2 pages).
SBIR Topic Summary: "Pro-Active Dynamic Accomodating Socket", SITIS archives topic No. OSD08-H18 (OSD); http://www.dodsbir.net/sitis/archieves_display_topic.asp?Bookmark=34570; downloaded and printed Mar. 25, 2013, U.S. A. (4 pages).
Initial and Interim Prostheses, Otto Bock Healthcare LLP, Prosthetics Lower Extremities 2008, (Feb. 2013) pp. 1-8, www.ottobockus.com/cps/rde/xbcr/ob_us_en/08cat_1.pdf.
Alley, "The High-Fidelity Interface: Skeletal Stabilization through Alternating Soft Tissue Compression and Release", Myoelectric Symposium 2011, New Brunswick, Canada, Aug. 14-19, 2011. (3 pages).
Andrysek, "Lower-limb prosthetic technologies in the developing world: A review of literature from 1994-2010", Prosthetics and Orthotics International, Cardiff, Wales, UK; Dec. 2010; 34(4): pp. 378-398. (21 pages).
Burgess, et al., "The Management of Lower-Extremity Amputations: Surgery: Immediate Postsurgical Prosthetic Fitting: Patient Care", Superintendent of Documents, U.S. Government Printing Office, Washington DC 20402 Publication prepared for the Prosthetic and Sensory Aids Service, Dept. of Medicine and Surgery, Veterans Administration, Washington, D.C., Aug. 1969. (129 pages).
Conn, "Materials Science: A Look at Some of the Substances on the Market for Device Fabrication", O&P Almanac, Jun. 2012, pp. 28-31; downloaded from http://www.allardusa.com/pdf/articles/Materials%20Science%20Article%20-%20June%202012%20O%26P%20Almanac.pdf. (4 pages).
Fairley, M. "M.A.S. Socket: A Transfemoral Revolution", The O&P Edge, Jun. 2004; downloaded from www.oandp.com/articles/2004-06-03.asp. (4 pages).

(56) References Cited

OTHER PUBLICATIONS

Gard, S.A. "Overview of Lower Limb Prosthetics Research", WRAMC and the VA Orthopedic & Prosthetic Workshop, Arlington, VA, Nov. 17 and 18, 2003, pp. 1-48. (49 pages).
Geil, M.D. "Consistency, precision, and accuracy of optical and electromagnetic shape-capturing systems for digital measurement of residual-limb anthropometrics of persons with transtibial amputation", Journal of Rehabilitation Research and Development, vol. 44, No. 4 (2007); pp. 515-524, U.S.A. (10 pages).
Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. (1 page).
Greenwald, et al., "Volume Management: Smart Variable Geometry Socket (SVGS) Technology for Lower-Limb Prostheses", JPO Journal of Prosthetics and Orthotics, vol. 15, No. 3 (2003), pp. 107-112, U.S.A. (6 pages).
Hong, et al, "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. (1 page).
Krouskop, et al., "Computer-aided design of a prosthetic socket for an above-knee amputee", Journal of Rehabilitation Research and Development, vol. 24, No. 2 (Spring 1987) pp. 31-38, U.S.A. (8 pages).
Manucharian, "An Investigation of Comfort Level Trend Differences Between the Hands-On Patellar Tendon Bearing and Hands-Off Hydrocast Transtibial Prosthetic Sockets", JPO: Journal of Prosthetics and Orthotics, Washington, D.C., U.S.A.; vol. 23, No. 3, 2011: pp. 124-140. (17 pages).
Prosecution Document,—PCT Search Report and Written Opinion dated Jun. 13, 2014, for International Application No. PCT/US2014/029773, (14 pages).
Prosecution Document—International Search Report, in connection with International Patent application No. PCT/US2012/064876, Feb. 19, 2013, (pp. 1-6).
Prosecution Document—Written Opinion, in connection with International Patent application No. PCT/US2012/064876, Feb. 19, 2013, (pp. 1-10).
Sanders, et al., "Residual limb volume change: Systematic review of measurement and management", Journal of Rehabilitation Research & Development, 2011, vol. 48: pp. 949-986, U.S.A. (29 pages).
Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 7, Issue 1; pp. 71-74, abstract. (1 page).
Smith, "Silver Linings for O&P Devices", The Academy Today, vol. 1, No. 4: Oct. 2005; downloaded from http://www.oandp.org/AcademyTODAY/2005Oct/7.asp. (4 pages).
Spaeth, JP , "Laser imaging and computer-aided design and computer-aided manufacture in prosthetics and orthotics", Physical Medicine and Rehabilitation Clinics of North America, Elsevier Publishing, Amsterdam, The Netherlands; Feb. 17, 2006 (1): 245-263, abstract. (2 pages).
Wilson JR. "A Material for Direct Forming of Prosthetic Sockets", downloaded from http://www.oandplibrary.org/al/1970_01_053.asp; downloaded Dec. 14, 2012. (4 pages).
Wu, et al, "CIR sand casting system for trans-tibial socket", Prosthet Orthol Int. Aug. 2003: 27(2): 146-52, abstract. (1 page).

\* cited by examiner

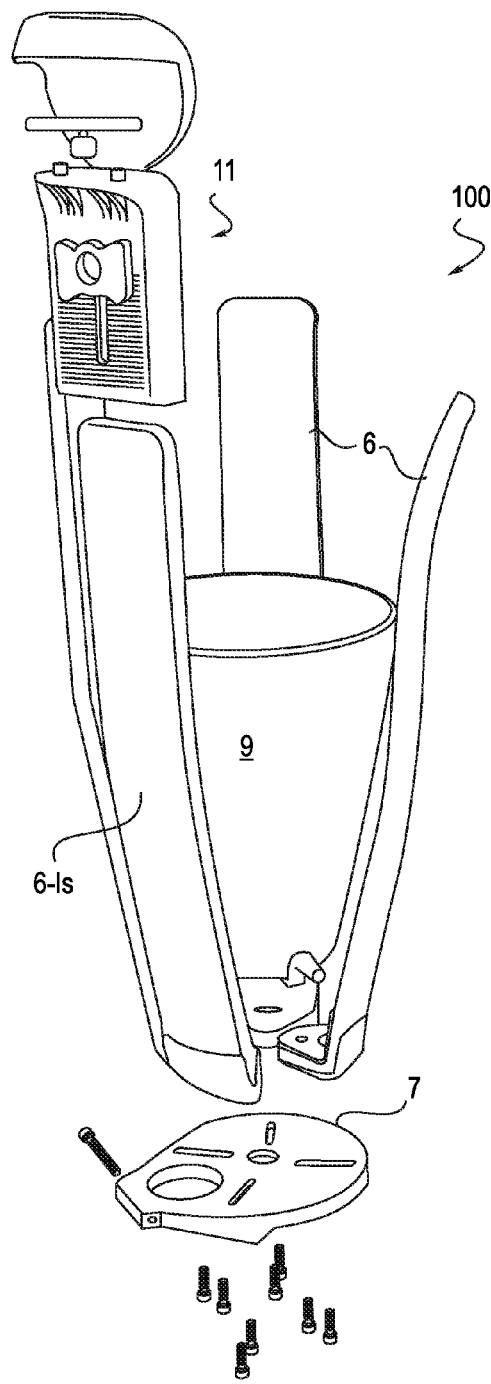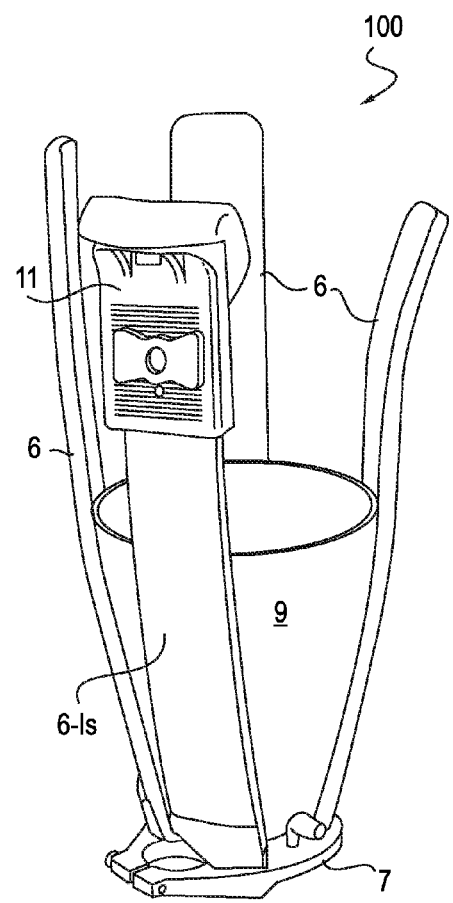
FIG. 6A
FIG. 6B

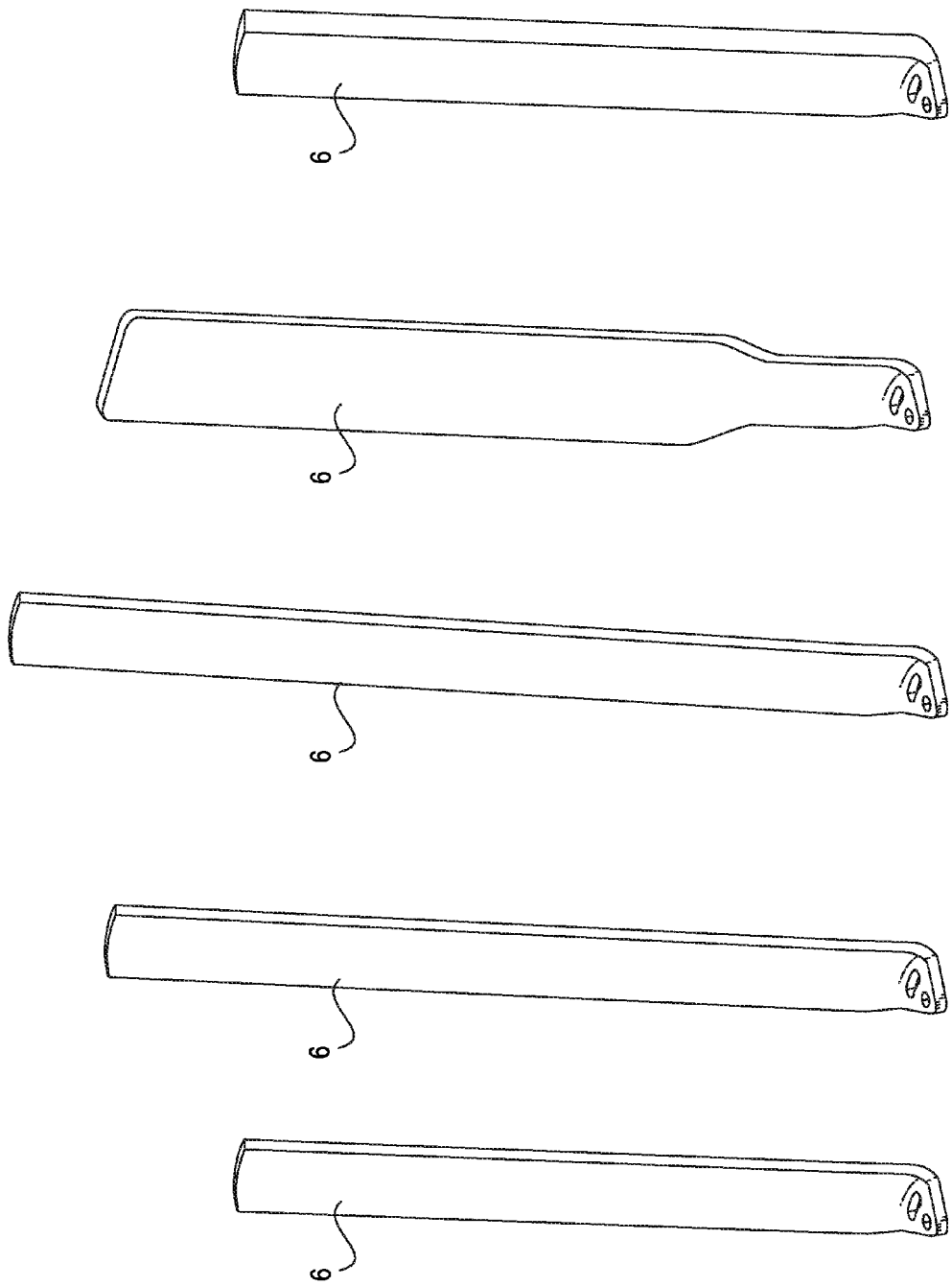

METHOD AND SYSTEM FOR ASSEMBLY OF A MODULAR PROSTHETIC SOCKET BASED ON RESIDUAL LIMB METRICS

CROSS-REFERENCE TO RELATED APPLICATIONS

This application claims priority to U.S. Provisional Patent Application No. 61/916,579, entitled "Method and system for assembly of a modular prosthetic socket based on residual limb metrics," filed on Dec. 16, 2013; 62/007,742, entitled "Apparatus and method for transferring a digital profile of a residual limb to a prosthetic socket strut," filed on Jun. 4, 2014; and 62/045,433, entitled "Improvements for a modular prosthetic socket: soft good arrangements, hardware, and a flexible inner liner," filed on Sep. 3, 2014.

INCORPORATION BY REFERENCE

All publications and patent applications referenced in this specification, including the above-listed patent applications, are hereby incorporated fully by reference herein, to the same extent as if each such individual publication or patent application were specifically and individually indicated to be so incorporated by reference.

FIELD OF THE TECHNOLOGY

The present technology relates to the field of prosthetic and orthotic systems and devices. More particularly, the technology relates to assembling an individually fitted, modular prosthetic socket and the logistics of information and component flow associated with its delivery to a patient.

BACKGROUND

The fabrication of a prosthetic socket typically occurs either in a local prosthetic clinical facility or in a commercial fabrication facility. The fabrication in a local prosthetic facility is very patient-specific and one-by-one; current methods are labor intensive and require highly skilled craftsmen and prosthetics. Prosthetic sockets made in such facilities typically fit the patient quite well, at least in a conformal sense, but can be deficient in terms of adjustability.

The fabrication process in a prosthetic facility is typically done completely in-house, and will now be elaborated on to convey a sense of its complexity and one-by-one character. The process begins with a prosthetist evaluating a patient's condition and needs, and taking measurements of the patient's residual limb. The prosthetist then casts a negative mold of the residual limb with casting tape. The resulting negative mold is filled with Plaster of Paris and allowed to harden. The negative cast is then peeled off to reveal the newly formed positive mold. The prosthetist may then modify the positive mold in an effort to create a form that best supports the creation of a limb socket that distributes pressure optimally on the residual limb when the socket is worn. The prosthetic socket, itself, is then built up by laminating layers of polymer material over the positive mold. Finally, the positive mold is broken and removed from within the fabricated socket, and the prosthetic socket may then be cut or further modified to better fit the residual limb.

Additional steps of the prosthetic socket fabrication process may include making and integrating flexible inner liners, locking mechanisms, alignment mechanisms, and other components, to create the final product. When fabrication of the socket is complete, the socket is typically tested on the patient for fit and for the patient's sense of how it feels and works. Although a few minor modifications of the socket are possible at this stage, such modifications are very limited, and the shape of the socket at this stage is the key factor in determining how well the socket will fit the residual limb and, thus, how comfortable the patient will be when wearing the prosthetic. As the ability to modify the shape and fit of the socket after fabrication in order to better accommodate the residual limb is very limited, it is common practice to make a number of "check sockets" or "diagnostic sockets," from which the best option is chosen as the final product for the patient.

Various aspects of this conventional prosthetic fabrication process, as practiced in local prosthetic clinics and shops, are less than satisfactory. The central role of physical molds in the fitting process and the transfer of size and shape information from the residual limb to the final prosthetic socket product is a limiting technological factor. The fabricating process itself can take a month or more, and is an inexact process. And although the finished prosthetic socket product may be apparently quite satisfactory at first, it is still substantially fixed in form and cannot be easily modified, if at all.

The residual limb itself, however, is not fixed in form. In fact, the residual limb often changes shape and condition radically, both in the short term and the long term. First of all, even if a prosthetic socket seems to fit perfectly in a prosthetist's office, the socket may rub or place pressure on the patient's residual limb during daily activity over the days and weeks that follow. Additionally, patients often lose or gain weight rather quickly as a result of their amputations, thus causing the residual limb to grow or shrink. Similarly, as patients use their residual limbs with their prosthetic devices, they may build muscle and/or portions of the residual limb may change shape due to stresses placed on it during use. Finally, as the patient ages, the residual limb will continue to change, in response to continued use and environmental conditions. Using currently available techniques for making prosthetic sockets, any time a significant change is needed in a socket for a patient, the only solution is to start the process again from step one and make a brand new socket.

In a commercial prosthetic fabrication facility, prosthetic sockets are made at a larger scale with at least some aspects of modern assembly methods. Typically, however, even such commercial facilities use manufacturing techniques that are very craft-like and are quite time and labor intensive. Importantly, sockets are not made for specific patients, but rather in a limited range of sizes, with limited sizing and configuration options. Even with adjustability options, typical commercial sockets still remain substantially fixed in shape and circumferential dimensions, particularly at their distal end. As described above, residual limbs and patient needs can change significantly over time, and the adjustability options in commercial prosthetic sockets are often not up to the challenge.

Based on the shortcomings of currently available prosthetic socket manufacturing techniques described above, it would be advantageous to have improved techniques for making prosthetic sockets. Ideally, such techniques would facilitate the manufacture of highly customized prosthetic sockets tailored to the specifics of each patient, while also allowing for larger production, scalable manufacturing. These manufacturing techniques would also need to provide prosthetic sockets of very high quality, durability, and ideally adjustability. Various embodiments of prosthetic sockets that may lend themselves to the manufacturing techniques described herein are described by the assignee of the present application in U.S. patent application Ser. No. 13/675,761 (Pub. No. US 2013/0123940), filed on Nov. 13, 2012; and Ser. No. 14/213,788, filed on Mar. 14, 2014. Both of these references are incorporated in their entireties herein.

Improved prosthetic socket manufacturing methods would also ideally facilitate the process required for prosthetists, physicians and most importantly patients. Such methods should reduce the amount of time required for a patient to receive a finished prosthetic socket from the first visit to a physician's or prosthetist's office. It would also be ideal if physicians and prosthetists could easily order and quickly receive prosthetic sockets and if patients did not have to undergo multiple fittings, adjustments and the like at the physicians' or prosthetists' offices. At least some of these objectives will be met by the embodiments described herein.

SUMMARY

Embodiments of the technology are directed toward methods and systems of fabricating and assembling a modular prosthetic socket for a residual limb of a patient. Examples described and depicted herein generally refer to prosthetic sockets appropriate for serving a patient with an amputation of a lower limb, and more particularly to a transfemoral (above knee) amputation or a knee-disarticulation (through the knee) amputation.

In one embodiment, a method is directed toward providing a modular prosthetic socket for a residual limb of a single patient (or at least one patient, or a patient taken one at time). Embodiments of this method include receiving digital data defining a three-dimensional digital profile of the residual limb; and based at least in part on the received digital profile, selecting prosthetic socket components from component-specific inventories. The selected prosthetic socket components include multiple longitudinal struts, wherein each strut comprises a proximal end and a distal end, and wherein each strut comprises a thermoplastic-fiber composite material; one or more proximal brim members for attachment to the longitudinal struts at or near the proximal ends of the longitudinal struts; and a distal socket base to which the longitudinal struts attach at or near their distal ends. The method next includes providing the selected prosthetic components to an operator for assembling into the modular prosthetic socket, wherein the prosthetic socket, when assembled, defines an internal space substantially complementary to the profile of the residual limb of the patient.

In some embodiments of the method, receiving digital data includes receiving the data at a fabrication facility as conveyed from a clinical prosthetic facility.

In some embodiments of the method, at least one of the component groups includes at least one of multiple sizes or shapes of the respective component; in spite of such variation, appropriate components remain mutually connectable.

In some embodiments, the method further includes assembling the selected components together to yield the modular prosthetic socket. In some particular examples of these embodiments, assembling the selected components together includes making mechanical adjustments to any of the components or to connections between components that affect a configuration of the internal space defined by the prosthetic socket.

In some embodiments of the method, prior to the providing step, the method further includes thermally reforming at least one of the selected components to improve an overall fit of the prosthetic socket to the residual limb.

In some embodiments of the method, prior to the providing step, the method further includes packaging the selected components from inventories of components as a kit with instructions for use. And in particular examples of this embodiment, the method may further include sending the kit to a clinical prosthetics facility.

In some embodiments of the method, prior to the receiving step, the method may further include profiling the residual limb of the patient with regard to metrics of dimension and shape to yield the digital profile. In various exemplary embodiments, the metrics of dimension and shape may be acquired by any one or more of methods of manual measurements, tomography, magnetic resonance tomography, X-ray, ultrasound, radiofrequency, acoustic compliance, scanning, photography, photogrammetry, casting, or mapping with a three dimensional point reference device a three-dimensional digital or physical representation of the residual limb. More generally, the acquired digital data may be acquired by any suitable method or modality that yields data sufficient to provide a satisfactorily complete and accurate profile of the residual limb.

Particular embodiments of the method may further include rendering the digital profile to be operable for downstream aspects of the method, such as any of selecting assembleable prosthetic socket components or thermally reforming components. With regard to sites and locations of operators engaged in the method, in some embodiments, the profiling and rendering steps are performed in a clinical prosthetics facility, and the method may further include transmitting the digital profile of the residual limb to a prosthetic socket fabrication facility.

In some embodiments of the method, based at least in part on the digital profile and prior to the selecting step, the method may further include fabricating components from at least one of the recited prosthetic socket component groups. And in particular embodiments, prior to the concluding providing step, the method may include shipping the selected components from a fabrication facility to a clinical prosthetics facility.

To review aspects and examples of the logistics of the flow of digital information and physical items, typically digital information is acquired, processed into operable form, and then transmitted from a clinical facility to one or more fabrication sites. The one or more fabrication sites, in various embodiments, may ship any of prosthetic socket components, prosthetic socket kits, or fully assembled prosthetic sockets to a clinical facility.

In another embodiment of the technology, a method is directed toward providing a modular prosthetic socket for a residual limb of a single patient (or at least one patient, or a patient taken one at time), concluding with step in which the modular prosthetic socket is assembled. Accordingly, embodiments of this method include receiving digital data defining a three-dimensional digital profile of the residual limb; and based at least in part on the received digital profile, selecting prosthetic socket components from component-specific inventories. The selected prosthetic socket components include multiple longitudinal struts, wherein each strut comprises a proximal end and a distal end, and wherein each strut comprises a thermoplastic-fiber composite material; one or more proximal brim members for attachment to the longitudinal struts at or near the proximal ends of the longitudinal struts; and a distal socket base to which the longitudinal struts attach at or near their distal ends. The method next includes assembling the modular prosthetic socket from the selected prosthetic components, wherein the prosthetic socket, when assembled, defines an internal space substantially complementary to the profile of the residual limb of the patient.

In some embodiments of the method, receiving digital data includes receiving the data at a fabrication facility as conveyed from a clinical prosthetic facility.

In some embodiments of the method, at least one of the component groups includes at least one of multiple sizes or shapes of the respective component; in spite of such variation, appropriate components remain mutually connectable.

In some embodiments of the method, at assembling the selected components together includes making mechanical adjustments to any of the components or to connections between components that affect a configuration of the internal space defined by the prosthetic socket.

In some embodiments of the method, prior to the assembling step, the method further includes thermally reforming at least one of the selected components to improve an overall fit of the prosthetic socket to the residual limb.

In some embodiments of the method, prior to the assembling step, the method further includes packaging the selected components from inventories of components (typically, along with instructions for use) as a kit. And in particular examples of this embodiment, the method may further include sending the kit to a clinical prosthetics facility.

In some embodiments of the method, prior to the receiving step, the method may further include profiling the residual limb of the patient with regard to metrics of dimension and shape to yield the digital profile. In various exemplary embodiments, the metrics of dimension and shape may be acquired by any one or more of methods of manual measurements, tomography, magnetic resonance tomography, X-ray, ultrasound, radiofrequency, acoustic compliance, scanning, photography, photogrammetry, casting, or mapping with a three dimensional point reference device a three-dimensional digital or physical representation of the residual limb.

Particular embodiments of the method may further include rendering the digital profile to be operable for downstream aspects of the method, such as any of selecting assembleable prosthetic socket components or thermally reforming components. With regard to sites and locations of operators engaged in the method, in some embodiments, the profiling and rendering steps are performed in a clinical prosthetics facility, and the method may further include transmitting the digital profile of the residual limb to a prosthetic socket fabrication facility.

In some embodiments of the method, based at least in part on the digital profile and prior to the selecting step, the method may further include fabricating components from at least one of the recited prosthetic socket component groups. And in particular embodiments, prior to the concluding providing step, the method may include shipping the selected components from a fabrication facility to a clinical prosthetics facility.

In yet another method embodiment of the technology, a method is directed toward providing multiple modular prosthetic sockets for the residual limb of multiple patients, i.e., a modular prosthetic socket for each of a plurality of patients, each prosthetic socket customized for a particular patient. Accordingly, embodiments of this method include receiving digital data that define three-dimensional profiles of the residual limbs of the multiple patients; and based at least in part on the received digital profiles, selecting prosthetic socket components from component-specific inventories for assembly of multiple modular prosthetic sockets. The selected prosthetic socket components include multiple longitudinal struts, wherein each strut comprises a proximal end and a distal end, and wherein each strut comprises a thermoplastic-fiber composite material; one or more proximal brim members for attachment to the longitudinal struts at or near the proximal ends of the longitudinal struts; and a distal socket base to which the longitudinal struts attach at or near their distal ends. The method next includes providing the selected prosthetic components to at least one operator, wherein each of the modular prosthetic sockets, when assembled from the selected prosthetic components, defines an internal space substantially complementary to the profile of the residual limb of one of the multiple patients.

In some embodiments of the method, receiving digital data includes receiving the data at a fabrication facility as conveyed from a clinical prosthetic facility.

In some embodiments of the method, at least one of the component groups includes at least one of multiple sizes or shapes of the respective component; in spite of such variation, appropriate components remain mutually connectable.

In some embodiments, the method further includes assembling the selected components together to yield the modular prosthetic sockets, one for each of the multiple patients. In some particular examples of these embodiments, assembling the selected components together comprises making mechanical adjustments to any of the components or to connections between components that affect a configuration of the internal space defined by any of the prosthetic sockets.

In some embodiments of the method, prior to the providing step, the method further includes thermally reforming at least one of the selected components to improve an overall fit of at least one of the prosthetic sockets to the residual limb of at least one of the patients.

In some embodiments of the method, prior to the providing step, the method further includes packaging the selected components from inventories of components as at least one kit with instructions for use, the at least kit being intended for a particular patient among the multiple patients. And in particular examples of this embodiment, the method may further include sending the kit to a clinical prosthetics facility.

In some embodiments of the method, prior to the receiving step, the method may further include profiling the residual limb of the multiple patients with regard to metrics of dimension and shape to yield the digital profile of each of the multiple patients. In various exemplary embodiments, the metrics of dimension and shape may be acquired by any one or more of methods of manual measurements, tomography, magnetic resonance tomography, X-ray, ultrasound, radiofrequency, acoustic compliance, scanning, photography, photogrammetry, casting, or mapping with a three dimensional point reference device a three-dimensional digital or physical representation of the residual limb of each of the multiple patients.

Particular embodiments of the method may further include rendering the digital profiles to be operable for downstream aspects of the method, such as any of selecting assembleable prosthetic socket components or thermally reforming components. With regard to sites and locations of operators engaged in the method, in some embodiments, the profiling and rendering steps are performed in one or more clinical prosthetics facilities, and the method may further include transmitting the digital profile of the residual limb to one or more prosthetic socket fabrication facilities.

In some embodiments of the method, based at least in part on the digital profiles and prior to the selecting step, the method may further include fabricating components from at least one of the recited prosthetic socket component groups. And in particular embodiments, prior to the concluding providing step, the method may include shipping the selected components from a fabrication facility to a clinical prosthetics facility.

Embodiments of the technology further include a system for providing modular prosthetic sockets for residual limbs of multiple patients. Embodiments of the system include an inventory of prosthetic socket components assembling multiple modular prosthetic sockets, the assembling based at least in part on a digital profile of the residual limb. The prosthetic socket components include multiple longitudinal struts, wherein each strut includes a proximal end and a distal end, and wherein each strut includes a thermoplastic-fiber composite material; one or more proximal brim members for attachment to the longitudinal struts at or near the proximal ends of the longitudinal struts; and a distal socket base to which the longitudinal struts attach at or near their distal ends. Embodiments of the system further include a data storage device storing instructions for selecting patient-specific prosthetic socket components from the inventory; and a processor configured to execute the instructions to perform a method.

Embodiments of the method performed by the system include receiving digital data defining three-dimensional profiles of the residual limbs of the multiple patients; and based at least in part on the digital data, selecting the patient-specific prosthetic socket components from the inventory for assembly of multiple modular prosthetic sockets, wherein each of the modular prosthetic sockets, when assembled from the selected prosthetic components, defines an internal space substantially complementary to the profiles of the residual limbs.

In some embodiments of the method performed by the system, receiving digital data comprises receiving the data at a fabrication facility as conveyed from a clinical prosthetics facility.

In some embodiments of the system, at least one of the component groups includes at least one of multiple sizes or shapes of the respective component; and in spite of such variation, appropriate components remain mutually connectable.

In some embodiments of the method performed by the system, the method further includes assembling the selected components together to yield the modular prosthetic sockets. And in some of these embodiments, the assembling the selected components together includes making mechanical adjustments to any of the components or to connections between components that affect a configuration of the internal space defined by any of the prosthetic sockets.

In some embodiments of the method that include an assembling step performed by the system, prior to the assembling step, further comprises thermally reforming at least one of the selected components of one of the modular prosthetic sockets to improve a fit of one of the prosthetic sockets to the residual limb of one of the patients. And in some of these embodiments, prior to the assembling step, the method further includes packaging the selected components from inventories of components as a kit, along with instructions for use. And in some of these embodiments, the method further includes sending the kit to a clinical prosthetics facility.

In some embodiments of the method performed by the system, prior to the receiving step, the method further includes profiling the residual limb of the multiple patients with regard to metrics of dimension and shape to yield the digital profile of the residual limb of each of the multiple patients. In some of these embodiments, the metrics of dimension and shape are acquired by any one or more of methods of manual measurements, tomography, magnetic resonance tomography, X-ray, ultrasound, radiofrequency, acoustic compliance, scanning, photography, photogrammetry, casting, or mapping with a three dimensional point reference device a three-dimensional digital or physical representation of the residual limb. And in some of these embodiments, the method further includes rendering the digital profiles to be operable for any of selecting assembleable prosthetic socket components or thermally reforming components.

In some of these embodiments, the profiling and rendering steps are performed in a clinical prosthetics facility, the method further comprising transmitting the digital profiles of the residual limbs to a prosthetic socket fabrication facility.

In some embodiments of the method performed by the system, the method, based at least in part on the digital profiles and occurring prior to the selecting step, the method further includes fabricating components from at least one of the prosthetic socket component groups. And in some of these embodiments, the method further comprises shipping the selected components to a clinical prosthetics facility.

BRIEF DESCRIPTION OF THE FIGURES

FIG. 6A is an exploded, perspective view of a modular prosthetic socket, showing various hardware components and a distal cup, according to one embodiment;

FIG. 6B is an assembled, perspective view of the modular prosthetic socket of FIG. 6A;

FIGS. 9A-9E are perspective views of five modular thermoplastic-fiber composite struts, according to five embodiments, which vary in size, but have consistent connection features that allow assembly with other modular components into a prosthetic socket intended for a particular patient;

DETAILED DESCRIPTION

The subject matter of this application is related to U.S. patent application Ser. No. 13/675,761 (Pub. No. US 2013/0123940), entitled "Modular prosthetic sockets and methods for making same," filed on Nov. 13, 2012; and Ser. No. 14/213,788, entitled "Modular prosthetic sockets and methods for making and using same," filed on Mar. 14, 2012, the full disclosures of which are incorporated herein by reference. These patent applications describe various embodiments and details of the structure, modular assembly, thermoplastic-fiber composition, and associated methods of forming and reforming prosthetic socket components.

The present application is directed to methods and systems for the assembly of a complete individualized prosthetic socket for a lower limb in the context of scaled manufacturing methods. It is further directed to the role of digital data in driving and coordinating these methods within a system, and to delivering a modular prosthetic socket with an optimal, customized fit for each patient. Examples described and depicted herein generally refer to prosthetic sockets appropriate for serving a patient with an amputation of a lower limb, and more particularly to a transfemoral (above knee) amputation or a knee-disarticulation (through the knee) amputation. However, embodiments or aspects of the technology may also be suitable for providing a modular prosthetic socket for leg amputations that occur below the knee and for amputations of an arm above the elbow, at the elbow, and below the elbow.

Figure 1:
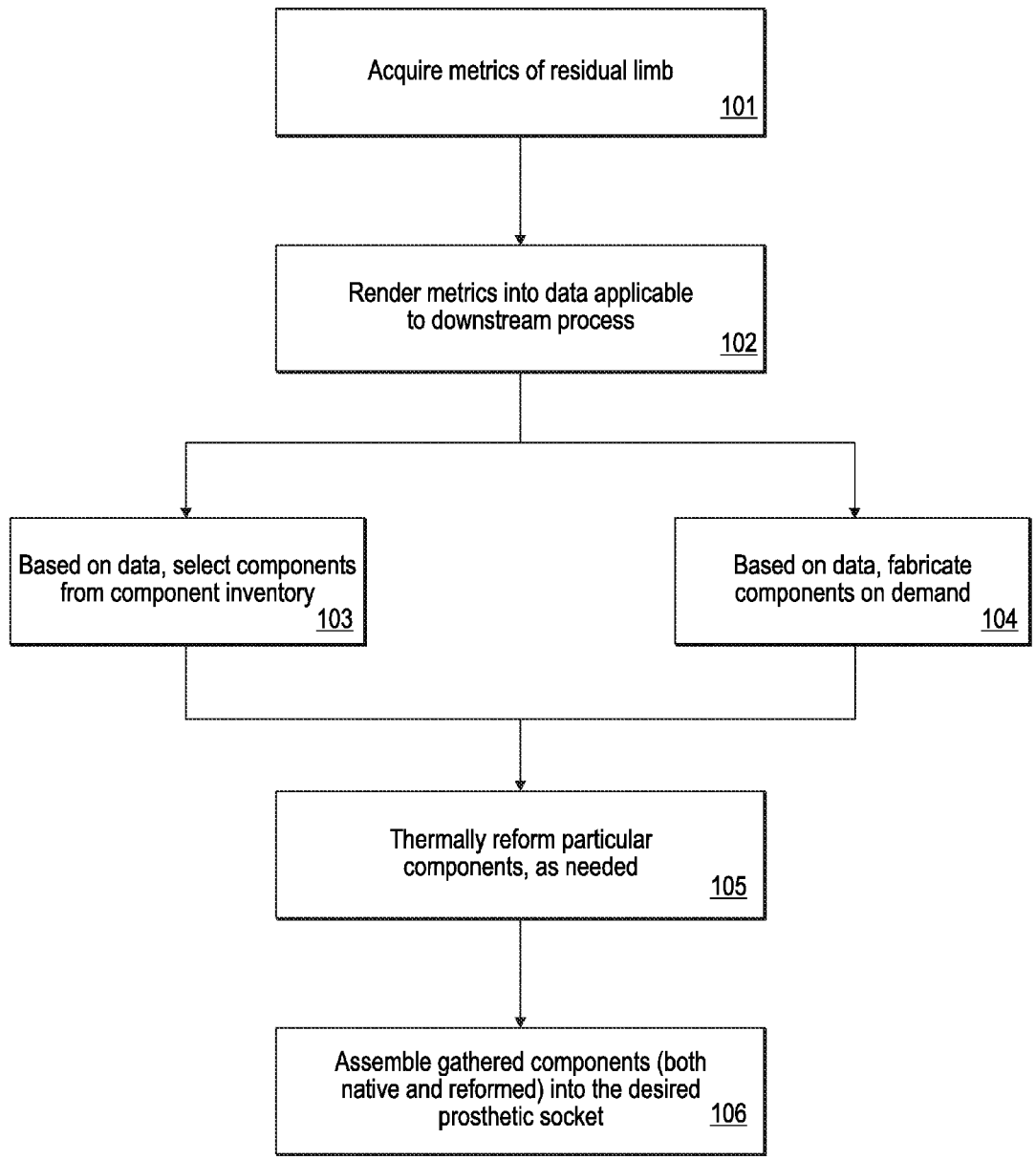
FIG. 1 is a flow diagram depicting a method for assembling a modular prosthetic socket based on measurements and/or a digitally captured profile of a patient's residual limb, according to one embodiment.
Figure 2:
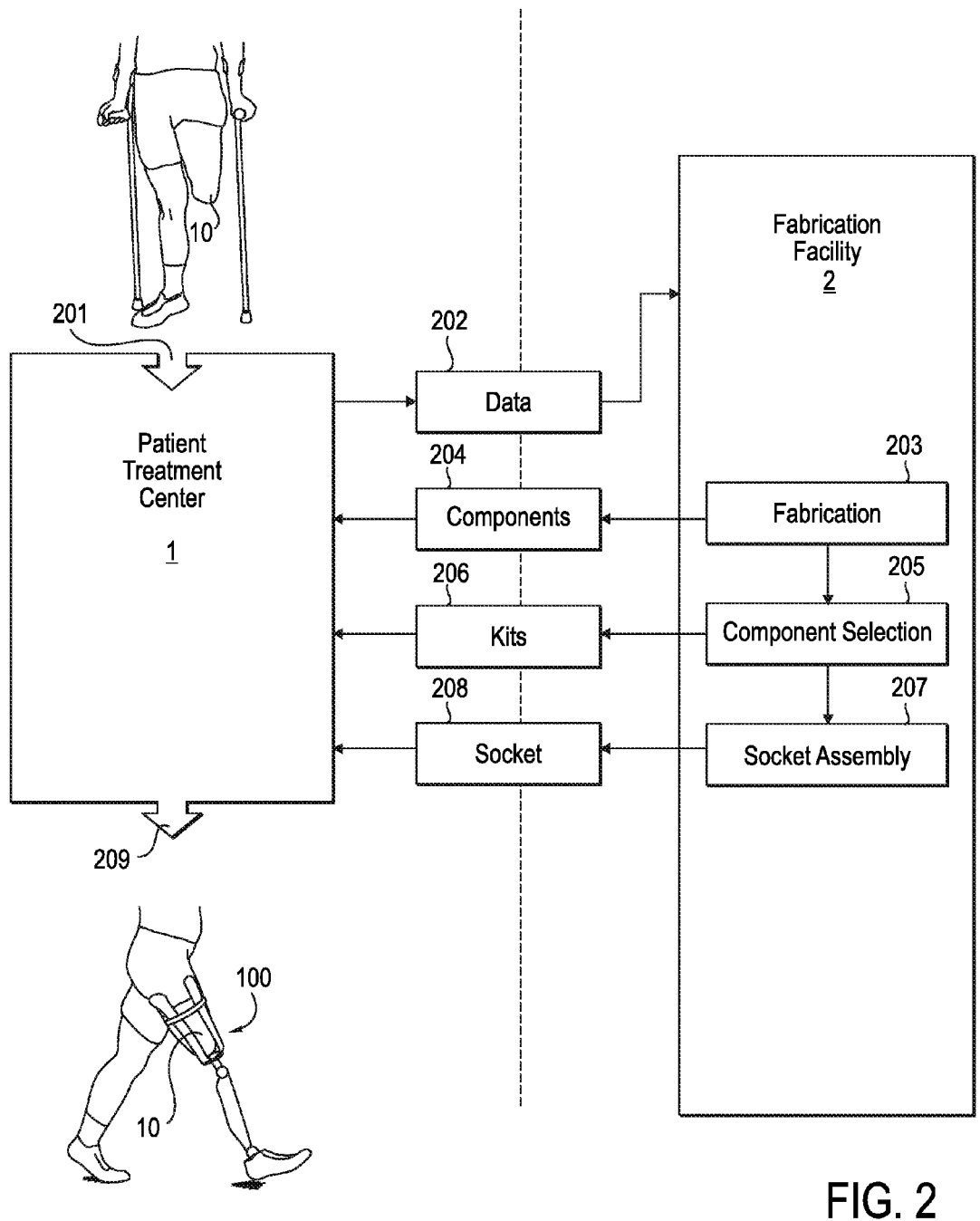
FIG. 2 is a schematic diagram that shows patterns of the flow of digital data, modular prosthetic socket components, modular prosthetic kits, and assembled modular prosthetic sockets between a patient treatment center and a fabrication site, according to one embodiment.
Figure 3:
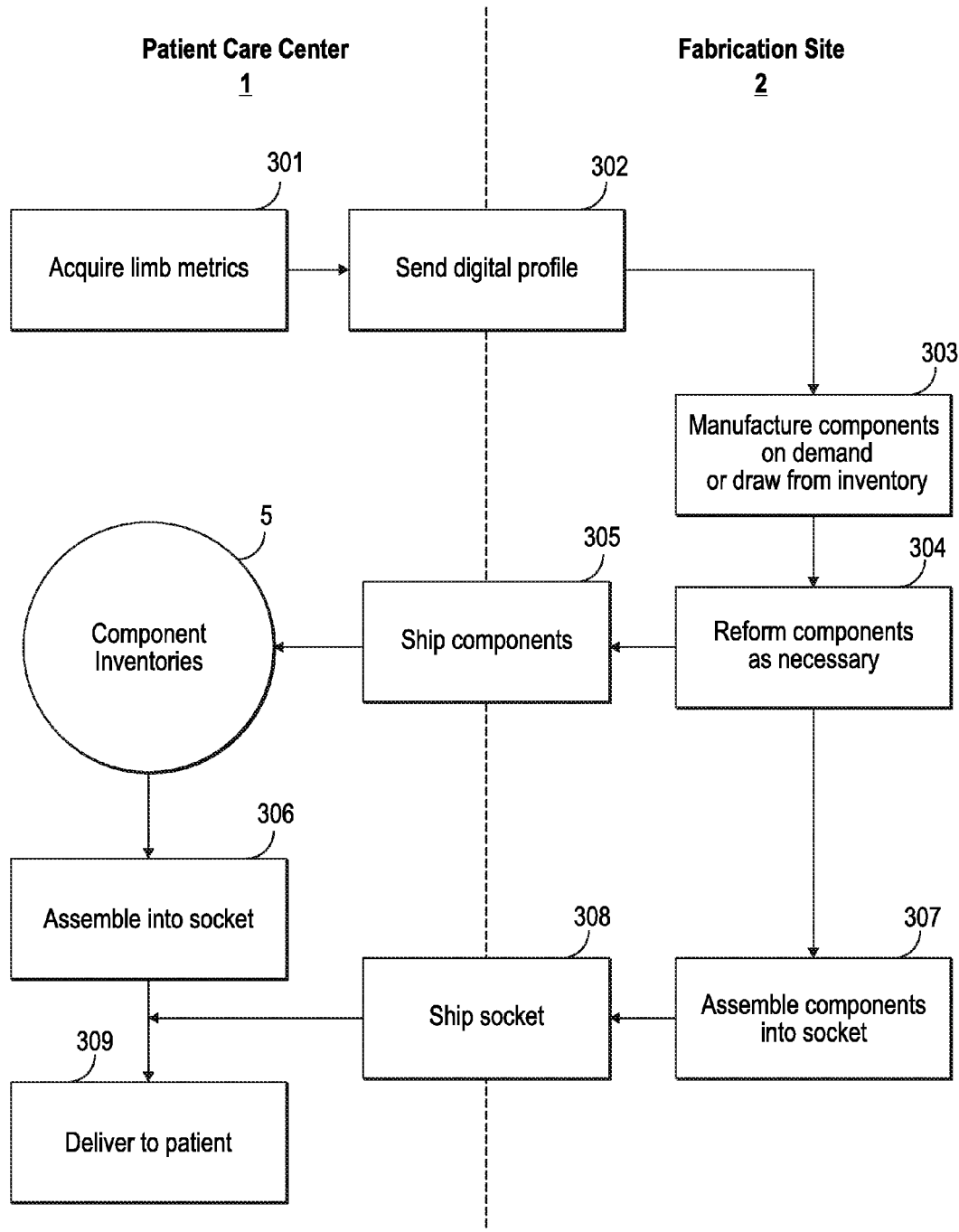
FIG. 3 is a flow diagram depicting a method for assembling a modular prosthetic socket based on measurements and/or a digitally captured profile of a patient's residual limb, including details of distribution of method steps between a prosthetic clinical facility and a fabrication facility, according to one embodiment.
Figure 4:
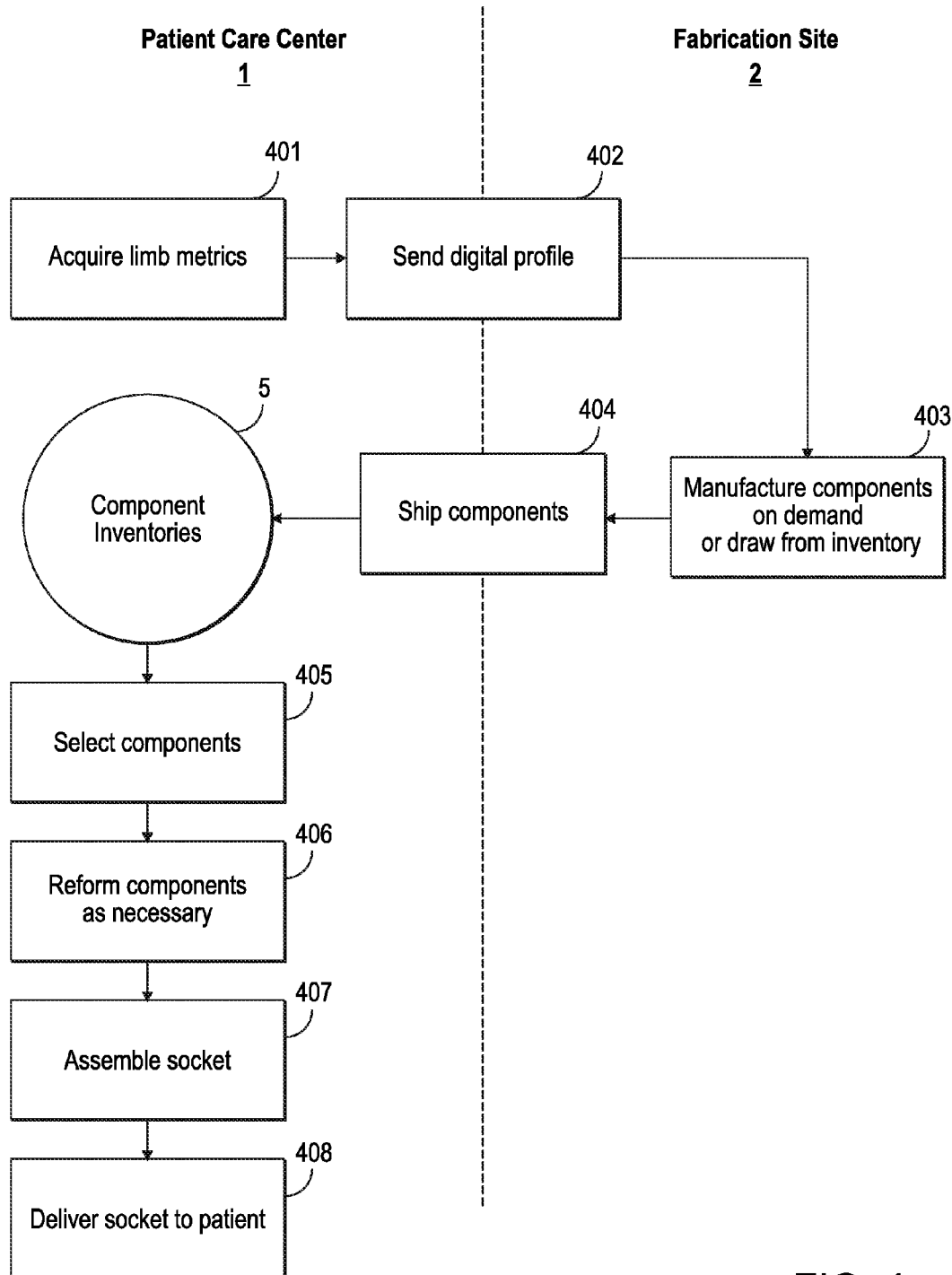
FIG. 4 is a flow diagram depicting a method for assembling a modular prosthetic socket based on measurements and/or a digitally captured profile of a patient's residual limb, including details of distribution of method steps between a prosthetic clinical facility and a fabrication facility, according to an alternative embodiment.
Figure 5:
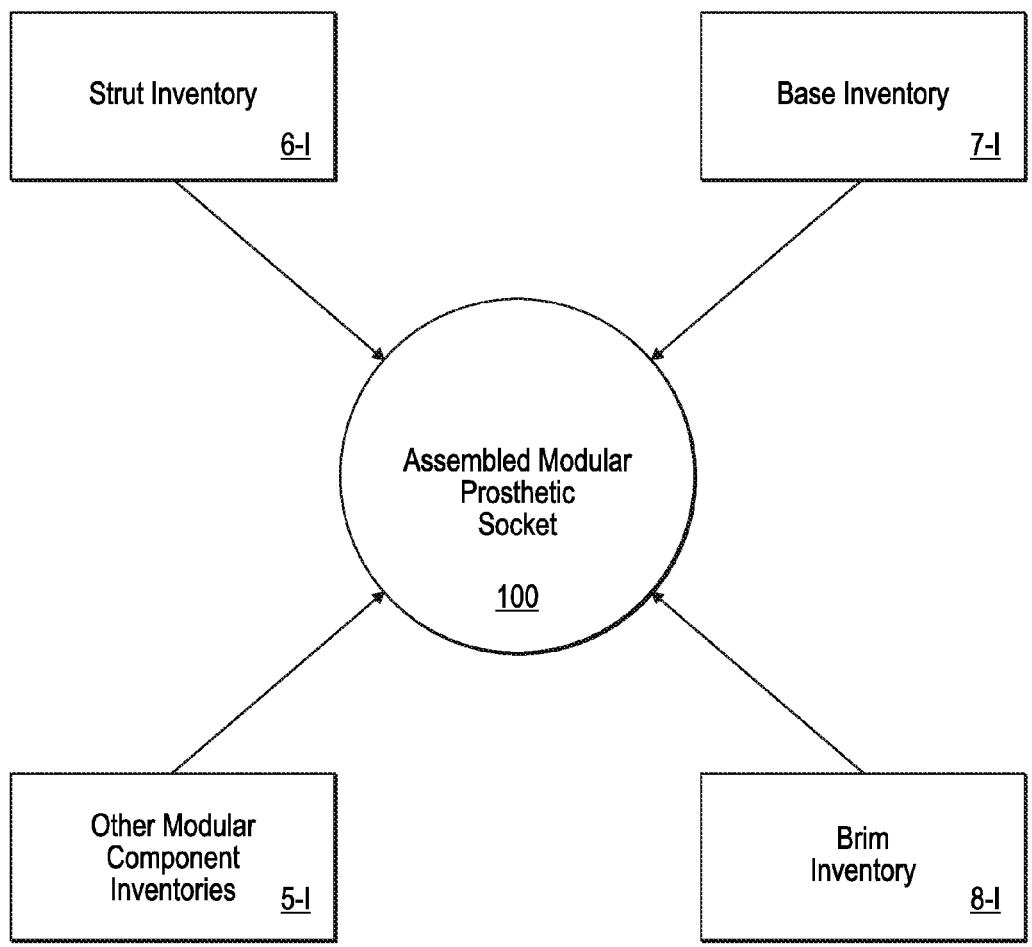
FIG. 5 is a schematic diagram of the assembly of a modular prosthetic socket from selected components, according to one embodiment.

Methods of mass scale fabrication, assembly, and delivery of a custom-fitted prosthetic socket to patients, per particular embodiments of the technology provided herein, occur or are typically implemented by operations in at least two sites, a patient care center 1 and a fabrication facility 2. FIGS. 1-5 show various aspects of systems and methods of fabrication and assembly of a modular prosthetic socket. FIG. 1 shows a method flow diagram that is absent any reference as to where steps of the method occur. FIG. 2 provides a general view of an example of a system and method where steps are distributed between a patient treatment center 1 and a fabrication facility 2. FIG. 3 shows a more detailed example of a system and method where most of the activity related to fabrication and assembly occurs at the fabrication site 1, with the option of assembly of a socket at patient treatment center 1. FIG. 4 shows a more detailed example of a system and method where other than the initial fabrication of components, a substantial amount of further fabrication activity, such as thermal reforming of components and assembly of the complete socket occurs at the patient treatment center 1. FIG. 5 is a schematic diagram of a system and method for assembling a modular prosthetic socket from inventories of modular component parts.

FIGS. 6A-10C show embodiments of a modular prosthetic socket and various components thereof. FIG. 11 is a schematic diagram of a system of mass customization. FIGS. 1-5, and the description thereof, make reference to a modular prosthetic socket and components thereof which are depicted in FIGS. 6A-10D. The modular prosthetic socket 100 includes multiple longitudinal struts 6, a distal base plate 7, a brim element 8, and a distal cup 9.

FIG. 1 shows steps that may be included in one embodiment of a method of assembling a modular prosthetic socket, as exemplified by embodiments such as those described herein, and as exemplified by systems that perform such methods. In Step 101, metrics of the residual limb are acquired that are sufficient to provide a digital profile of the residual limb. Typically, the residual limb is measured and/or digitally captured by a prosthetist to derive metrics of dimensions and contours of the portion of the residual limb that will be accommodated by a modular prosthetic socket. This step may include any one or more of scanning, photography, making use of photogrammetry, casting, or mapping with a three dimensional point reference device a three-dimensional digital or physical representation of the residual limb. Further, advanced methodologies such as, merely by way of example, any of tomography, magnetic resonance tomography, X-ray, ultrasound, radiofrequency, or acoustic compliance may be used. This step may also include "manual" measurements, such as may be made by any of a ruler, tape measure, calipers, or the like. For example, basic measurements such as circumference and length may be taken, including circumference at regular intervals throughout the length. A three dimensional profile of a residual limb, in addition to providing a representation of the surface of the limb, may further include a three dimensional representation of internal features as distinguished, for example, by varying tissue density as possessed, for example, by bone, fat, and muscle. Acquired metrics may be entered as data into any suitable medium, in any suitable format.

In typical method and system embodiments, data for residual limb metrics are entered into a database, wherein algorithms may be applied to the metrics that render the residual limb profile operable in downstream steps. An operable digital profile of a residual limb serves as input to a system (see FIG. 11). Operable downstream steps are formulated as instructions, and output relates to method steps taken in response to instructions, based on input (see FIG. 11). Methods relate variously to fabrication, configuring an intended modular prosthetic socket, thermally reforming components as needed, assembling the deliverable prosthetic socket, and making mechanical adjustments during the assembling, among others. As used here, "data" or residual limb "profile" refer to any form of data that originates in an initially acquired form of any suitable format that profiles the residual limb, and further refers to any digital form the originally acquired data take on later in a downstream processing step.

Step 101 typically occurs at a patient care site, which may be referred to variously as a patient care facility, a patient treatment site, a medical center, a prosthetic clinical facility, a clinical prosthetics facility, or a prosthetics shop, or any remix of these various terms. This site, however it is referred to, is where the patient and the prosthetist and technical team meet in person, where the patient is evaluated, where the patient's residual limb is profiled, and where ultimately, the patient is fitted with a complete modular prosthetic socket.

In Step 102, these metrics are rendered into data that can be applied toward further downstream steps in various method embodiments. Rendering of data typically involves the use of one or more software applications and the generation of a transmittable data profile or report. In another aspect, the data, once rendered transmittable and actionable by downstream processes, may be considered a specification for a fully assembled prosthetic socket that fits the residual limb. In yet another aspect, the data may be included in a larger transmitted digital package that constitutes a work order to gather appropriate modular components and assemble them into a complete prosthetic socket. The complete modular prosthetic socket that is desired or intended is a socket that provides an internal space that is substantially complementary to the residual limb of the patient. Step 102 typically occurs at a patient care site, such as a prosthetic clinical facility.

The data from Step 102 may then be directed either to Step 103, in which appropriate modular components are selected from inventories of components and/or (alternatively) the data may be directed toward Step 104 in which a fabrication facility 2 makes appropriate components on demand. By way of either Step 103 or Step 104, modular components are gathered that are, collectively, optimal for the assembly of a complete prosthetic socket that is intended to fit the digitally captured residual limb well. Step 103 typically occurs at a fabrication site, but in some instances may occur at a patient care site, such as a prosthetic clinical facility. Step 104 typically occurs at a fabrication site.

A fully assembled modular prosthetic socket circumscribes or defines an internal space that is substantially complementary to the dimensions and contours of the residual limb, as captured by the metrics taken by the prosthetist (Step 101) and rendered into transmissible data (Step 102). Other factors may contribute to the ultimate intended shape of the prosthetic socket, such as biomechanical factors or clinical factors associated with the particular patient and his or her residual limb.

In some instances, the fit of an assembled modular prosthetic socket may be improvable by a thermal reforming procedure, as in Step 105. Typically, this optional step is applied to individual modular components prior to final assembly of the prosthetic socket. Thus, at the conclusion of Step 105, a set of components has been gathered that will collectively form the intended modular prosthetic socket. The set of components may include original, native, or non-reformed components (i.e., components as they were originally fabricated, without further thermal-based modification), and it may also include thermally reformed components. By way of example, thermoplastic-fiber composite struts 6 (FIG. 9) in their original form are flat or substantially flat pieces. By way of a thermal reforming method, various contours may be applied to these originally flat pieces (see FIGS. 10A-10D) in order to contribute to the assembly of an intended prosthetic socket. Step 105 may occur either at a fabrication site 2 or at a patient care site 1, such as a prosthetic clinical facility.

In Step 106, the modular components, including any combination of (1) the direct products of Step 103 (selected from an inventory), or (2) Step 104 (made on-demand), or (3) the product of Step 105 (a thermally reformed component) are assembled together to create the intended complete modular prosthetic socket. The immediate products of Steps 103 and 104 may be considered initially formed components, i.e., direct or substantially direct products of manufacture). Manufacturing steps (not shown, but described in detail in U.S. patent application Ser. No. 14/213,788) typically include processes that thermally mold thermoplastic or thermoplastic-fiber composite materials into a particular component form. Products of Step 105 may be considered "reformed" components, whose shape (contour, angulation) differs at least to some degree from the component in its initially formed shape. Step 106 may occur either at a fabrication site or at a patient care site, such as a prosthetic clinical facility. Steps 105 (thermal reforming) or 106 (assembly), regardless of the site at which they occur, may be performed either by human operators or robotic operators, or by a combination of both.

In various embodiments of methods of manufacturing prosthetic socket components and assembling them into a modular prosthetic socket, method steps may be distributed between one or more sites or facilities. By way of example, one facility may be a prosthetic clinical facility or a patient treatment center 1, staffed by one or more professional prosthetists or trained specialists. A prosthetic facility may be characterized as a bricks and mortar style permanent facility, or it may be a mobile facility This clinical facility is typically the site where the patient engages the presently described system and method, and where the patient and the prosthetist, technical specialist or operator meet. There, the patient is evaluated for overall health issues and interviewed regarding physical lifestyle, biomechanical particulars, personal preferences, and any personal medical aspect of the patient that relates to the amputated limb or to life going forward with a prosthetic device. More particularly, the residual limb is evaluated and measured or profiled so as to yield a set of metrics that capture dimensions and contours of the residual limb. These metrics are subsequently converted by one or more software applications, as operated within a computer that renders the data applicable for downstream use as a specification for the assembly of a modular prosthetic socket, as well as driving associated methods that ultimately yield a custom-fitted socket for each patient.

A second facility, or any of several facilities, may be a fabrication center 2, where modular prosthetic socket components are manufactured. A fabrication facility may assume responsibility for all phases of manufacture of components from commercially available stock materials, and may include thermal reforming of components, as well as assembly of components into a finished product. Alternatively, fabrication of components may be distributed among several facilities, which may be dedicated to particular components, or to particular manufacturing steps. A fabrication facility may further include warehouse space, and full capabilities for shipping of components, kits, or finished product, and receiving raw materials. By way of another example, a third facility may be one that is involved in a subset of the manufacturing or assembly steps, or dedicated to particular logistical steps such as warehousing, shipping, or receiving. Further, patient treatment center 1 and any one or more of fabrication sites 2 need not be distant from each other; they are typically distinct and separated physical sites, but they may be next door to each other or even housed under the same roof. Their distinction relates less to their physical embodiment or location and more to their distinct roles and operations.

Embodiments of the system may include one or more software applications that facilitate communication and cohesion within the system, even as facilities may be geographically separate, or under separate ownership and control. By way of example, software that renders metrics of residual limb and shape into data that are useful downstream could be used both by prosthetic clinical facility and by a fabrication facility. By way of another example, software that controls logistics of sending components or finished product, or product billing codes, may usefully contribute to cohesion or functional integration within embodiments of a system, particularly one where aspects of clinical practice and product manufacturing and assembling are distributed among different entities. By way of still another example, software may generate electronic reports that can be added to a patient's medical record.

FIG. 2 is a schematic diagram of an embodiment of a system and method that shows basic patterns of the flow of digital data, modular prosthetic socket components, modular prosthetic components, modular prosthetic kits, and assembled modular prosthetic sockets between a patient treatment center 1 and a fabrication site 2. The term "fabrication facility" as used herein is term that may refer to one or more sites (separate, conjoined, or integrated) where component fabrication occurs, and further may include separate or associated facilities for component warehousing, component selection and packaging, and modular prosthetic socket assembly. Operations within fabrication facility 2 may be performed by highly skilled professionals, by technicians or operators, by automated robotic devices, or by any combination thereof. For simplicity in describing operations within the fabrication facility or any of its component functional units or sites, method steps will be recited as being performed by the facility itself.

As shown in FIG. 2, a patient initially engages (Step 201) the patient treatment center 1 when he or she is in need of a modular prosthetic socket to be fitted to his or her residual limb 10 and, in concluding at least an initial stage of engagement, walks away (Step 209) fitted with an assembled, fully customized, modular prosthetic socket. At later points in time, of course, the patient may return to patient treatment center 1 for medical care issues related to his or her residual limb, or for mechanical or fitting issues related to use of the prosthetic socket 100.

Between the initial Step 201 and final Step 209 of patient engagement, the patient care center 1 has conveyed (Step 202) digital data that profiles the residual limb to a fabrication facility 2. In turn, and based on the digital profile, fabrication facility 2 fabricates components (Step 203) and may ship (Step 204) the components to the patient treatment center 1 as components.

After fabrication of components (Step 203), alternatively, the fabrication facility 2 may select and gather (Step 205) components for a particular prosthetic socket, and ship (Step 206) the components as a kit back to patient treatment center 1.

After selecting and gathering (Step 205) components for a particular prosthetic socket, alternatively, the fabrication facility 2 may assemble (Step 207) the components into a complete modular prosthetic sockets and ship (Step 208) them to patient treatment center 1. In an optional step (not shown), components selected in Step 205 may be thermally reformed, according to the digital profile of the residual limb that were sent from patient treatment center 1 in order to improve the fit of fully assembled socket 100 to the patient's residual limb.

FIGS. 3 and 4 provide examples of embodiments wherein provided embodiments of a system and method for fabricating and assembling mass-produced custom-fitted modular prosthetic sockets are distributed among one or more facilities or sites. In both FIGS. 3 and 4, a patient care facility 1 (and method steps occurring therein) is depicted on the left side of the figure, and a fabrication site or facility 2 (and the method steps occurring therein) is depicted on the right side of the figure. A dotted line separates the territories represented by patient care facility 1 and fabrication facility 2. Digital profiles of the residual limb are sent (left to right, across the dotted line) from patient care facility 1 to fabrication facility 2 in steps 302 and 402. And components, kits, and fully assembled sockets are sent from fabrication facility 2 to patient care facility 1 (right to left, across the dotted line) variously in Steps 305, 308, and 404.

FIG. 3 shows an example of a system and method that, with the exception of patient engagement at a local prosthetic clinical facility, is substantially centered at a fabrication and assembly center 2. FIG. 4 shows an example of a system and method that is (with the exception of manufacturing of components) has a substantial amount of activity is centered within a local prosthetic clinical center 1. A typical local prosthetic clinical center capable of handling socket assembly responsibility includes a shop with basic functionalities, such as an inventory of components, tools and workspace for handling and assembling components into a complete prosthetic socket, and tools and devices for thermally reforming components as may be needed.

One of the main difference between the processes outlined in FIGS. 3 and 4 relates to where the thermal reforming of components and where assembly of the intended prosthetic socket occurs. In the example depicted in FIG. 3, these processes occur at a remote fabrication site or sites. In the example depicted in FIG. 4, these processes occur at a patient care site. FIGS. 3 and 4 are merely examples of how aspects of the provided system and method may be distributed among various facilities. The scope of the invention includes any combination or variation of these two examples.

FIG. 3 is a diagram of a system and method for the assembly and delivery of a prosthetic socket that is substantially centered at a fabrication center 2, the fabrication center being is in communication with- and working cooperatively with local prosthetic clinical facility 1. In Step 301, the residual limb is profiled by a prosthetist at a prosthetic clinical facility to derive metrics of dimensions and contours of the portion of the residual limb that will be accommodated by the prosthetic socket. This step may include any one or more of methods of scanning, photography, making use of photogrammetry, casting, or mapping with a three-dimensional point reference device a three-dimensional digital or physical representation of the residual limb, as well as traditional types of manual measurement. Step 301 may further include data processing in a software application to render the original metrics into data that can be used as desired product specifications, and drive downstream processes.

In Step 302, data that have been acquired and packaged appropriately for downstream processing in Step 301 are transmitted to a fabrication site 2. A fabrication facility 2 manufactures a range of modular prosthetic socket components, and may further include inventories of manufactured components. Sending the metrics in the form of profile of the residual limb to the fabrication facility may be accompanied by or used as an order for components with which to assemble a prosthetic socket, or by an order for a completely assembled socket.

In Step 303, accordingly, components, per the data transmitted in Step 302, are either fabricated on demand, or drawn from an existing inventory. Step 303 may further include gathering components together that will be ultimately used to assemble an intended socket, or alternatively, in the absence of a physical gathering, labeling them or identifying them in some manner as being assigned to a particular intended modular prosthetic socket.

In Step 304, based on data acquired in Step 301, particular components may be thermally reformed as may be necessary in order that the modular prosthetic socket optimally assume the intended conformation. In a typical thermal reforming process, a thermoplastic-fiber composite strut is reformed to have a shape that better conforms to a particular aspect of the patient's residual limb. The reforming of individual struts contributes to and optimizes the overall fit of the intended prosthetic socket, when assembled.

In Step 305, following Step 304, modular prosthetic components, both those in a "native" configuration (those that have not be subjected to thermal reforming) and those that have been thermally reformed, are physically gathered and shipped to patient care site 1 as a kit. The kit of components may reside in a local inventory until the patient returns to patient care facility 1.

Two alternative steps may follow from Step 304. In Step 305, as above, assembled components are shipped to patient care site 1, for assembly there. In Step 306, the modular prosthetic socket components are assembled into a complete socket at the fabrication site 2.

In Step 308, the fully assembled prosthetic socket is shipped from fabrication site 2 to patient care site 1. As in Step 305, the assembled prosthetic socket may temporarily reside in an inventory until the patient, for whom the socket is intended, comes to the patient care site for his or her next appointment.

In Step 309, a complete prosthetic socket, either as assembled at the patient care site 1 (as in Step 306) or as assembled at fabrication site 2 (as in Step 307), is delivered to the patient.

FIG. 4 is a diagram of a system and method for the assembly and delivery of a prosthetic socket that, compared to the depiction of FIG. 3, is more centered at a local prosthetic clinical facility 1 that is working in communication with and cooperatively with a remote fabrication facility 2. (Basic fabrication of components from stock materials remains located at fabrication site 2). In Step 401, the residual limb is measured or digitally profiled by a prosthetist to derive metrics of dimensions and contours of the portion of the residual limb that will be accommodated and supported by an intended modular prosthetic socket 100. This step may include any one or more of methods of scanning, photography, making use of photogrammetry, casting, or mapping with a three-dimensional point reference device a three-dimensional digital or physical representation of a patient's residual limb, or making use of manual measuring techniques. Step 401 may further include data processing in a software application to render the original metrics into data that can be used as desired product specifications and to drive fabrication processes.

In Step 402, data acquired and packaged appropriately for downstream processing in Step 401 are transmitted to a fabrication site 2. (These steps may be considered to be substantially equivalent to steps 101 and 102 of FIG. 1.) A fabrication facility 2 manufactures a range of modular prosthetic socket components, and may further include inventories of manufactured components. In Step 403, accordingly, components, per the digital profile data transmitted in Step 402, are either fabricated on demand, or drawn from an existing inventory. Step 403 may further include generally gathering the components and preparing them for shipment to the local patient care site 1.

In Step 404, the components either made on demand or selected from existing inventories, are shipped to patient care site 1, where they are received; these components may be held, at least transiently, in a local inventory 5.

In Step 405, the components that were shipped in Step 404 (according to data acquired in Step 401 and sent to the fabrication site in Step 403) are selected and readied for being assembled into an intended prosthetic socket.

Data acquired that profile the residual limb and subsequently modified for downstream processing are still present and actionable within patient care site 1. In Step 406, based on these data, particular components are thermally reformed as may be necessary or advantageous in order that the ultimate fully assembled prosthetic socket 100 optimally assume the intended conformation. In a typical thermal reforming process, a thermoplastic-fiber composite strut is reformed to have a shape that better conforms to a particular aspect of the patient's residual limb.

In Step 407, all necessary modular components are gathered and assembled into a complete modular prosthetic socket. In Step 408, the complete socket is delivered to the patient.

FIG. 5 is a schematic diagram of a system for assembling a modular prosthetic socket 100 from modular component parts. Arrayed around an assembled modular prosthetic socket are inventories of modular component parts. These inventories include a strut inventory 6-I, a distal base inventory 7-I, a brim inventory 8-I, and one or more inventories of other modular components 5-I. By way of example, other modular prosthetic socket components that may be modular in character include distal cups, strut connectors, tensioning elements, strut caps, and any other component included in the assembly of a prosthetic socket.

Examples of these components are depicted in figures that follow (embodiments of thermoplastic-fiber composite struts 6 are shown in FIGS. 9A-10D; embodiments of distal bases 7 are shown in FIG. 7, and embodiments of brims 8 are shown in FIG. 8). FIGS. 6A-6D depict a modular prosthetic socket 100 in several forms.

Inventories may also be generally referred to as "groups" or "collections" of components. These are non-limiting examples of modular components that may be used in the assembly of a modular prosthetic socket. Depending on circumstance and context, an inventory may be an actual physical inventory, or it may be a virtual or catalogue-based inventory. Inventories may also be used to package kits of components, or alternatively, a kit may itself also be considered a small inventory. Inventories of modular components typically include like components, with portions such as connecting sites in common, but otherwise including variations in size and/or variations in shape. In some instances, modular components may also differ from each other in material composition.

FIG. 5 may also be interpreted as a diagram depicting a method of assembling a modular prosthetic socket in that components may be selected from such inventories (5-I, 6-I, 7-I, and 8-I) and assembled together to create a modular prosthetic socket 100 of desired size and shape. As used herein and per embodiments provided, a modular prosthetic socket is a socket that includes one or more modular components, and by such inclusion, the possible modular prosthetic sockets that can be assembled therefrom vary in size and/or shape.

As described above, and as shown in FIGS. 1-5, an approach to the mass-customization and delivery of modular prosthetic sockets, particularly suitable for above-knee or knee-disarticulation amputations is provided. Production steps can be distributed among one or more sites (e.g., a clinical facility 1 and one or more fabrication facilities 2), each site assuming responsibility for one or more aspects of the ultimate delivery of a prosthetic socket 100 to a patient. Traditional and conventional approaches to fabricating prosthetic sockets, as discussed in the Background section, can have a high degree of customization and fit the patient well, but the methods of fabrication are not scalable. There are commercially available prosthetic sockets, manufacturable as units at some degree of scale, but in general, these prosthetic sockets are not modular in construction, and they are limited in terms of adjustability, particularly at the distal end.

Mass customization, as used herein, refers generally to a form of manufacturing in which custom, patient-specific products are provided in relatively large quantities or on a large scale. In various embodiments, systems and methods for providing mass customization of prosthetic sockets may enable a large range of prosthetic socket sizes and shapes to be delivered from a limited range of components and may also enable manufacturing of modular components at a large scale. The mass customization techniques described herein for providing modular prosthetic sockets rely on several underlying technologies, including:

1. Modularity: the modular character of the prosthetic socket assembly as built from individual components; the interconnectability of the individual components (despite otherwise variation in any of size, shape, or composition) and their mass producibility with high quality consistency.

2. A longitudinal strut-based structure that supports the creation of complex shapes from multiple simple parts.

3. Mechanical adjustability of the assembled socket 100, including, in particular, adjustability of the arrangement of longitudinal struts 6 on a distal base 7, which is typically done during assembly, but can be redone as needed. Further aspects of mechanical adjustability include manipulation by the patient of tensioning systems within the brim 8 of an assembled prosthetic socket 100.

4. Thermal reforming of the longitudinal struts 6, so as to assume a form more suitable for optimal fit and biomechanical functionality of assembled prosthetic socket 100, as a whole.

5. Digital capture of residual limb profile, and processing of the digital capture so as to provide actionable input in downstream selection, fabrication, thermal reforming processes, and mechanical adjustments.

6. The cooperative roles of a prosthetic clinic site 1 and one or more fabrication sites 2.

Among the features of the methods and systems shown in FIGS. 1-5 is a modular concept, based on relatively few modular components (e.g., including one or more of a distal base, multiple struts, a proximal brim, as well as distal cups), each component being available in a range of sizes and or shapes. A modular strut-based prosthetic socket structure has been achieved by breaking down the complex shape (that captures the residual limb as a whole) into several simply shaped struts, each strut needing to capture only a portion of the residual limb shape, the struts collectively capturing the shape as a whole. By assembling such modular components together, prosthetic sockets 100 having a large range of sizes and shapes can be created.

The range of sizes and shapes of an assembled prosthetic socket 100 is expanded or amplified by factors beyond what might be anticipated as feasible only through the use of several modular components. For example, the fact that four struts are typically used in the assembly, by itself, amplifies the range of possible sizes and shapes of a prosthetic socket, as each strut may selected and shaped independently from the other struts. Further, as described elsewhere herein, and in detail in U.S. patent application Ser. No. 14/213,788, the thermoplastic-fiber composite struts can be thermally reformed, thus improving the fit for an individual patient, but more generally expanding the range of prosthetic socket sizes and shapes possible from a set of modular components. Still further, features of the attachment of the struts to the distal base are independently adjustable in terms of their radial distance from the center of the distal base, and the struts are further independently pivotable such that their circumferential position can be varied.

By all these various factors, embodiments of a modular prosthetic socket can assume a very large range of sizes and shapes so as to be customizable for the residual limbs, which, of course, exist in a very large range of sizes and shapes. The modular components, themselves, are small in number, simple in shape, and readily manufacturable at large scale, with a high level of consistency and quality control. Thus, with these factors taken together, an approach to mass-producible, highly customized modular prosthetic sockets is provided.

FIGS. 6A-10C show embodiments of a modular prosthetic socket 100 and various modular components thereof. Modular componentry is generally characterized in terms of groups of components that vary in any of size, shape, or any aspect of configuration, but retain consistent connection features that allow components selected from these groups, collectively, to be assembled together to form a complete modular prosthetic socket 100. Accordingly, a fully assembled modular prosthetic socket 100, by virtue of varying constituent components will, itself, be able to assume or be configured in a range of sizes and shapes. Modular components included herein include struts 6, distal base plates 7, proximal brims 8, and distal cups 9. Struts 6 and base plates 7 may be generally referred to as hardware because of their metal and/or hard thermoplastic-fiber composite material compositions. Distal base plate embodiments 7 may also be referred to simply as a distal base; the distal term referring to the structural position of the component within the socket.

Embodiments of the technology are directed broadly to systems, and methods that are amenable to mass customization of deliverable prosthetic sockets. Such embodiments include a prosthetic socket assembly even if it includes only one of the components (as enumerated herein) has character that is modular as described herein. Embodiments of the technology further include any prosthetic socket assembly that includes at least one component that is modular in character (as described herein), even if such component is not directly analogous to any of the modular components described herein. Further, while typical embodiments of longitudinal struts, as provided herein, include a thermoplastic-fiber composite composition, the technology includes prosthetic sockets having struts made by non thermoplastic materials such as metals, or by thermoplastic materials without the fiber aspect of the composition. Strut structures comprising metal, even without the properties afforded by thermoplastics, may still be bent to assume an altered and desired shape. Strut structures comprising thermoplastic but lacking fiber may still be thermally reformed to assume a desired shape.

Distal cups 9, their thermoplastic composition and associated methods of making and reforming by direct molding against a distal end of a residual limb are described in detail in referenced U.S. Provisional Patent Application No. 62/045,433. Distal cups 9, as with other modular components may be maintained in groups or inventories of components, the distal cup embodiments varying in any one or more of size, shape, and composition. Some distal cup embodiments may include a thermoplastic composition that is amenable to thermal reforming at relatively low temperatures that can be tolerated against the body, particularly if protected by a thin thermal barrier. In these embodiments, accordingly, an inventory of distal cups that vary in size (e.g., small, medium, large) or shape (e.g., short, medium, tall) can be heated to a point of pliability, placed on the distal end of the residual limb, and be directly molded thereto, creating a highly customized fit.

Brims 8 may be considered soft goods because of their generally softer and compliant composition of fabric, and pliable plastic composition. Strut sleeves 13 may also be considered soft goods. Distal cups 9 have occupy a middle ground between hard and soft. All components (hardware, soft goods, and distal cup) participate, at least to some degree, in bearing weight and distributing pressure away from what would otherwise be focal points of pressure between the prosthetic socket and the residual limb. Hardware components form the main structural frame of the socket. Soft goods, in general, distribute pressure away from the structural frame, and provide an interface suitable for direct or close contact with the residual limb of the patient. A single label identifier will be used in referring to these various enumerated modular components for simplicity, their variability in size and/or shape notwithstanding. Similarly, modular prosthetic socket identifier 100 will be used in referring to prosthetic sockets regardless of the size, shape, or number of components shown in any particular figure.

FIG. 6A is an exploded view of a modular prosthetic socket 100, showing various modular hardware components and a modular distal cup 9. Various key structural modular elements, such as multiple longitudinal thermoplastic-fiber composite struts 6, a distal base plate 7, and a distal cup 9 are arranged in an exploded view. These components each may be selected from a group or inventory of modular cohorts, respectively, that vary in any of size or shape. In spite of such variation, the size and configuration of connective features that allow assembly to neighboring components remain constant. Inasmuch as modular prosthetic sockets 100 are assembled from components that vary in size and shape, so too, are assembled sockets, themselves, highly variable in terms of size and shape. FIG. 6B shows a view of a modular prosthetic socket 100, as assembled from various modular various hardware components and a distal cup 9, as enumerated in the description of FIG. 6A.

Figure 6C:
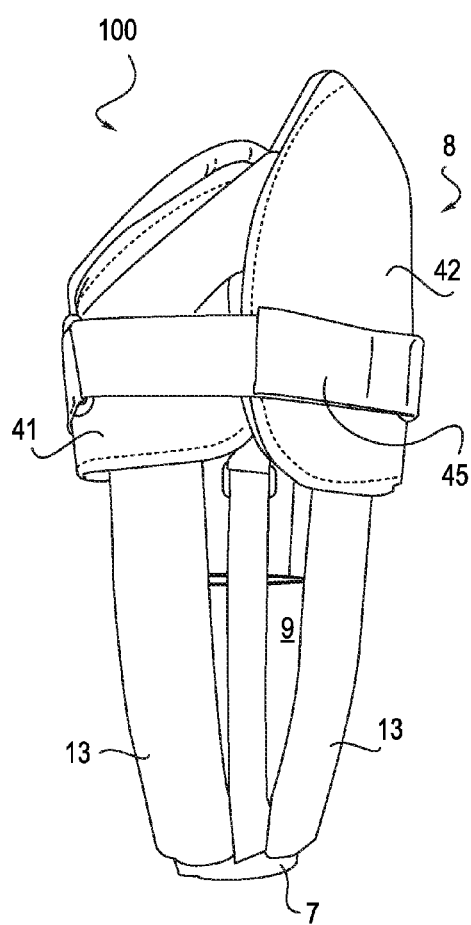
FIGS. 6C and 6D are an anterior view and a posterior view, respectively, of the modular prosthetic socket of FIGS. 6A and 6B, including a proximal brim, according to one embodiment.
Figure 6D:
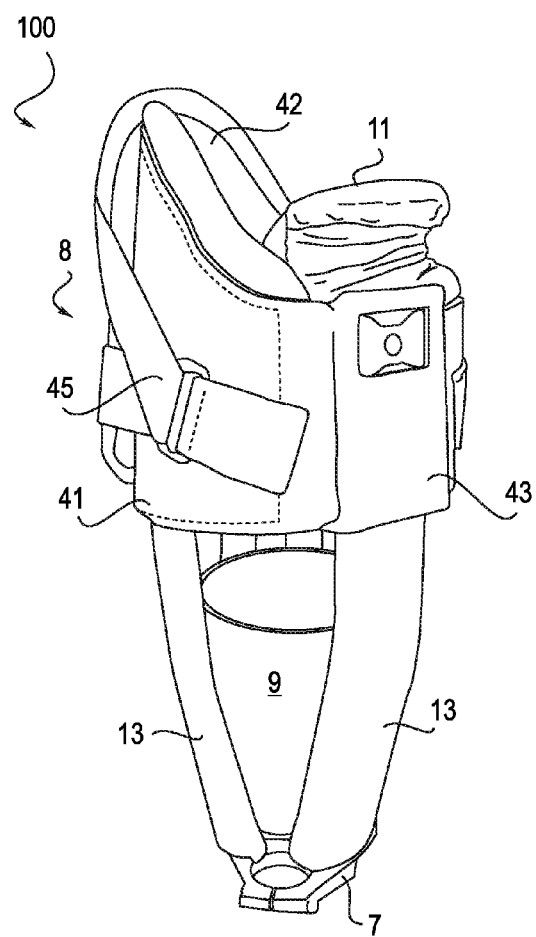

FIGS. 6C-6D show an anterior view and a posterior view, respectively, of a modular prosthetic socket 100, as assembled from various modular components enumerated in the description of FIG. 6A, but further including soft good elements, a proximal brim 8 and strut sleeves 13. An ischial seat 11 (also seen in FIGS. 6A and 6B) is shown telescopically positioned at the distal end of a strut 6-I (the ischial strut) positioned so as to engage the ischium of the patient. Brim 8 embodiments include a butterfly piece 41 and a trochanteric pad piece 42, an adjustable tensioning system 43, and an ischial strut pocket 44 that accommodates the distal portion of ischial strut 6-Is. Brim features are further detailed in FIGS. 8A-8C. An adjustable ischial seat 11 is positioned at the proximal end of strut 6-Is.

The adjustability of telescopically arranged ischial seat 11 is a particularly important feature for customized fitting. This is a mechanical adjustment that can be initially fixed by a prosthetist when fitting the patient, but the patient can very easily make this adjust without help. Further, the seat, itself, may vary modularly in size and shape, and accordingly is a feature that contributes to the mass customization that allows excellent fitting from modular components. By way of further explanation, the ischial seat allows the distribution of body weight that would otherwise be transmitted through the distal end of the residual limb to be taken up by the pelvis as a whole. Mechanical adjustability allows the patient to distribute weight bearing responsibility between the distal end of the residual limb and the pelvis, at will.

FIGS. 7A-7D show several modular distal base embodiments that vary in size and shape or configuration, but have consistent connection features that allow assembly with other modular components into a prosthetic socket intended for a particular patient. Strut slots 32 are dimensionally consistent among all variations, and are configured to host distal ends 21 of struts 6 (see FIGS. 9A-10C). Bolts 33 (see FIG. 9H) through the distal ends of struts are able to slide within the slots, but are securely positionable at any point within the slot by a locking arrangement at the distal surface of the base (not shown). By this mechanism, the shape and volume circumscribed by (defined by, or enclosed by) socket 100 is highly adjustable.

Figure 7A:
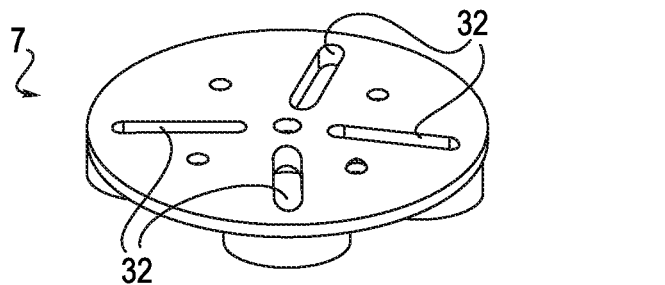
FIGS. 7A-7D are perspective views of four modular distal bases for a prosthetic socket, according to four embodiments, where the four modular bases vary in size, but have consistent connection features that allow assembly with other modular components into a prosthetic socket intended for a particular patient.

FIG. 7A shows a distal base modular embodiment 7 in which a distal prosthetic component (not shown) is connectable a central site at the on the distal aspect (not shown) of distal base 7. In these terms, the default alignment of a distal prosthetic component with respect to distal base 7 may be said to have "zero offset". This configuration differs from distal base embodiments 7 shown in FIGS. 7B-7D, all of which have a distal component connection site (in the form of a threaded receptacle 31 that is offset from the center of distal base 7. Distal base embodiments of FIGS. 7B and 7C have the same diameter, and may be considered (for example) a "medium" size. Distal base embodiment 7 of FIG. 7D, in contrast is a "large" size.

Figure 7B:
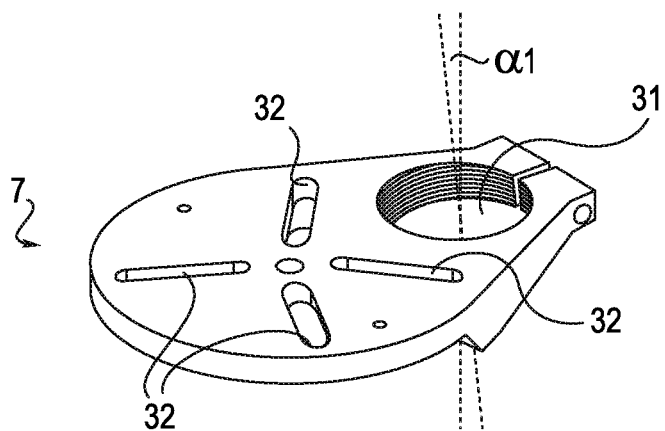
Figure 7C:
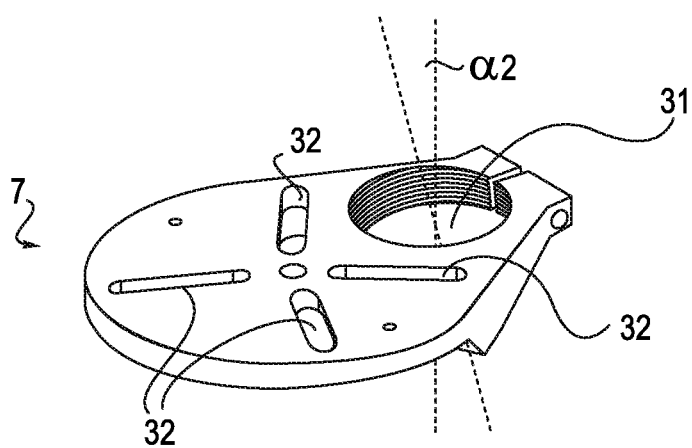
Figure 7D:
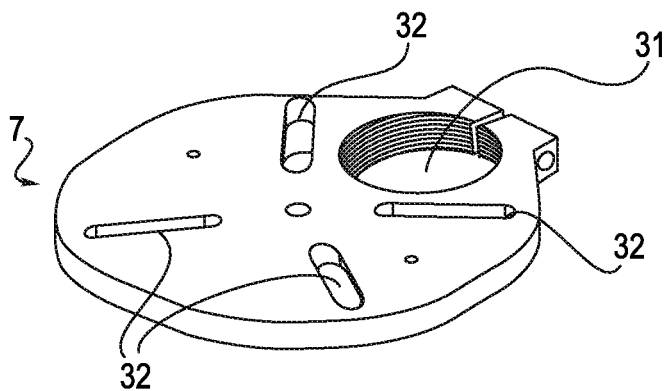

It can be seen that, in spite of differences in base diameters, the length and other dimensional aspects of strut slots 32 are identical in each distal base embodiment shown in FIGS. 7A-7D. In comparing embodiments of FIG. 7C vs. FIG. 7D, it can be seen that strut slots 32 in FIG. 7D are displaced outward from the center of the distal base in comparison to those of FIG. 7D. By this radially outward displacement, the volume defined by struts 6 attached to distal base 7 is larger than the volume of sockets the could be assembled from distal bases shown in FIGS. 7A-7C.

Distal base modular embodiments 7, as shown in FIGS. 7B and 7C appear to have substantially the same size and general configuration, however there is a difference. Distal component threaded receptacle 31 can be configured at angles that vary from vertical. This angle determines the default angle of flexion that the distal prosthetic component has with respect to prosthetic socket 100, as a whole. In the examples shown, the angle $\alpha 1$ (FIG. 7B) is small compared to angle $\alpha 2$ (FIG. 7C). From the foregoing description of distal base 7 embodiments, at least some of the different configurations not only of the base itself, but determinative of consequential variations in the prosthetic socket configuration as a whole, and the alignment relationship of the socket and a distal component all follow from modular variations of distal base 7. In spite of these configuration variations, the component connecting features (prosthetic strut slots and distal component connecting sites) remain constant.

Figure 8A:
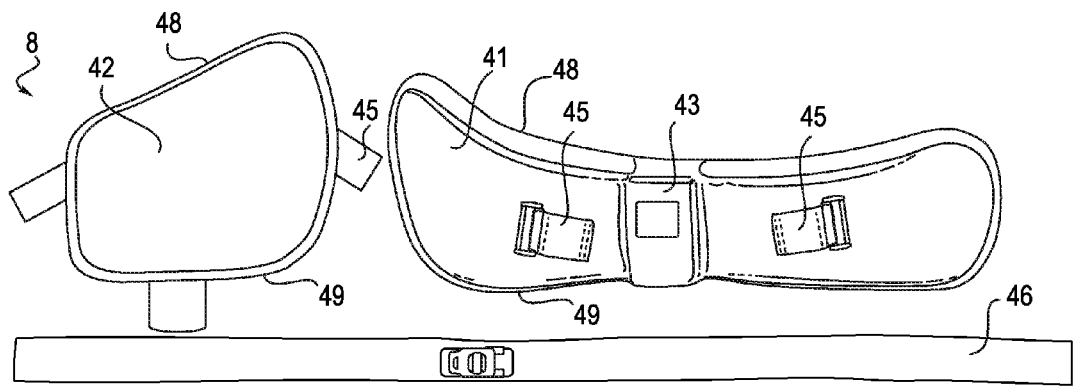
FIGS. 8A-8C are front views of three modular brim members, according to three embodiments, which vary in size, but have consistent connection features that allow assembly with other modular components into a prosthetic socket intended for a particular patient.
Figure 8B:
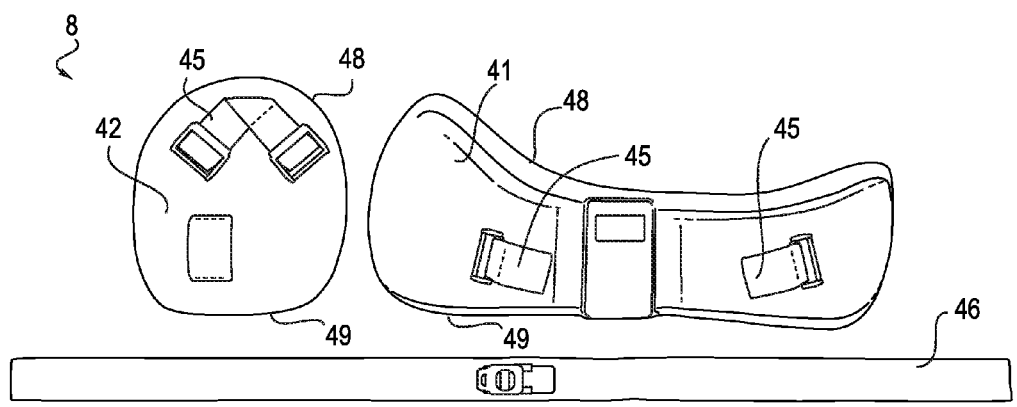
Figure 8C:
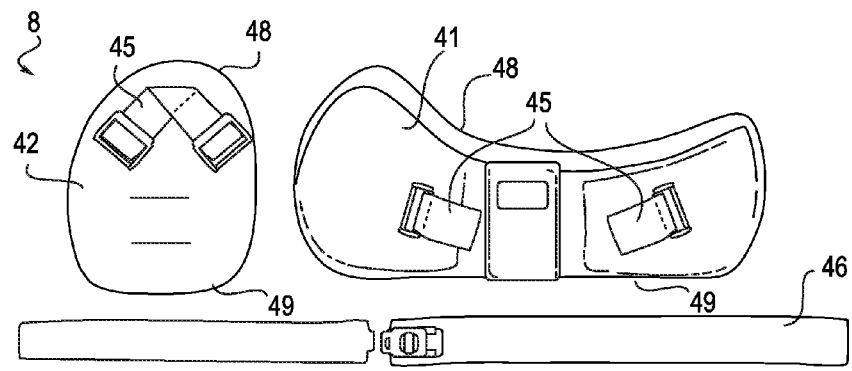

FIGS. 8A-8C show several modular brims 8 that vary in size, but have consistent connection features that allow assembly with other modular components into a prosthetic socket intended for a particular patient. FIG. 8A shows a large size brim; FIG. 8B shows a medium size brim; and FIG. 8C shows a small size brim. Brims 8 include two major components, a butterfly piece 41 and a trochanteric pad piece 42. To clarify terminology as used herein, a brim 8 refers to the component in its entirety. A brim, in its entirety, may include more than one or more component pieces or members. In the examples of brim embodiments provided herein, brim 8 includes two major component pieces or members (butterfly piece 41 and a trochanteric pad piece 42). Brim 8 may also be referred to as a "proximal brim", a term that emphasizes its relative position within prosthetic socket 100 as a whole.

Butterfly portion 41 and trochanteric pad 42 each have a proximal edge 48 and a distal edge 49. The brim embodiments 8 in these figures are shown in a flat, laid out configuration, the external surface being shown except for the trochanteric pad 42 of FIG. 8A, which exposes the internal surface, which is a smooth in contrast to external surfaces which are fitted with connecting features. (The rolled brim configuration is shown in FIGS. 6C and 6D.)

In addition to butterfly portion 41 and trochanteric pad portion 42, brim embodiments 8 include connecting and tensionable adjusting systems that connect to the two major pieces when placed in a wrap around configuration (as in FIGS. 6C and 6D). These connecting systems include a ladder lock based tensioning macro-adjustment tensioning system 45 and a ratchetable belt tensioning micro-adjustment system 46. An ischial strut channel 43 is seen in the mid section of butterfly piece 41; this channel hosts the ischial strut 6-Is as seen in FIGS. 6D and 6D. Other strut enclosure pockets (not visible in these views) accommodate the other struts 6 of the modular prosthetic socket 100.

Figure 9F:
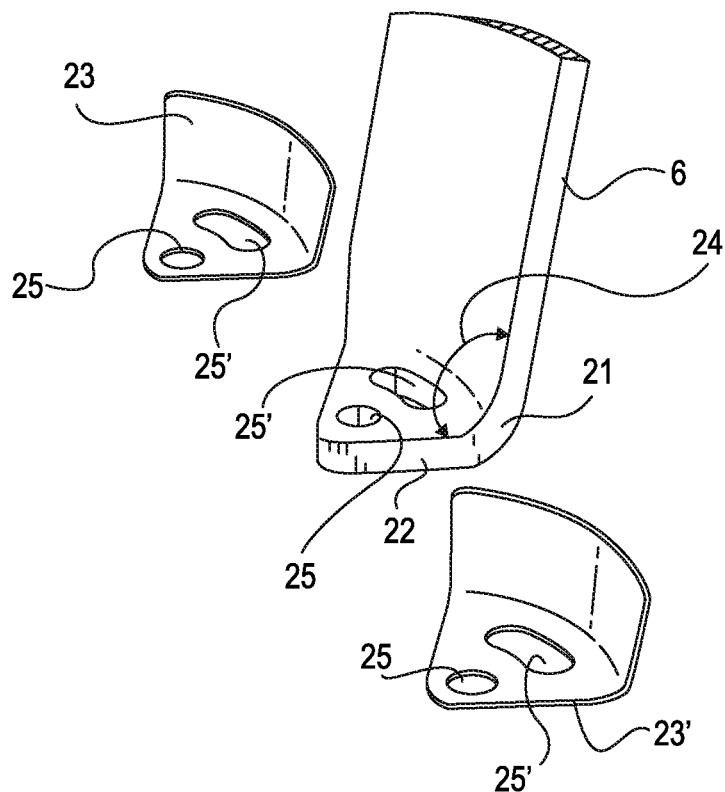
FIGS. 9F-9G are perspective exploded and assembled views, respectively, of a distal end of a modular thermoplastic-fiber composite strut with metal cladding over the internal and external surfaces, according to one embodiment.
Figure 9G:
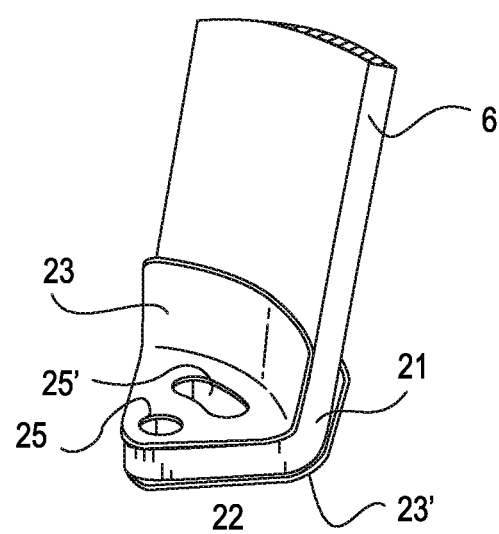

FIGS. 9A-9E shows several modular thermoplastic-fiber composite strut embodiments 6 that vary in size, but have consistent connection features that allow assembly with other modular components into a prosthetic socket intended for a particular patient. FIGS. 9F and 9G show detail of the distal portion 21 of struts 6, which is configured for attachment to distal base 7. Struts can be dimensionally characterized by length, width, and thickness. Struts 6 of FIGS. 9A-9C have identical width and thickness, but vary in length. Strut 6 of FIG. 9A is relatively short; strut 6 of FIG. 9B is of medium length; and strut 6 of FIG. 9C is relatively long. Strut 6 of FIG. 9D has a length identical to that of FIG. 9C, but is wider. Strut 6 of FIG. 9E differs from the other struts depicted by having greater thickness. In spite of these dimensional variations, all struts 6 of FIGS. 9A-9E have identical attachment configurations at their distal ends, by which the struts attach to a distal base.

FIGS. 9F and 9G show details of the distal portion 21 of strut embodiments 6. Distal portions 21 of struts 6 have a flat distal surface 22 that engages against the surface of distal base 7 and a take off contoured portion of a variable angle 24 with respect to flat distal surface 22. Variation in angle 24 provides one of the several modular variations in shape or configuration of struts 6; angle 24 variations may be stocked as inventory components, or imparted as needed by thermal reforming. Distal end 21 of strut 6 typically includes metal cladding pieces on both sides of the strut, an internal cladding piece 23 and an external cladding piece 23'. Bolt holes 25 and 25' extend through each of the internal cladding piece 23, flat distal end surface 22 of strut 6, and external cladding piece 23'. Bolt hole 25 is round hole positioned at an inner radial position with respect to distal base 7 when attached thereto; bolt hole 25' has a kidney bean shape and is positioned radially outward from bolt hole 25. This configuration of boltholes allows the strut 6 to pivot within the angular range provided by bolt hole 25' while being fixed at the position defined by bolt hole 25. This angular pivot is yet another particular example of configurational variation of assembled socket 100 provided by modular assembly and adjustable mechanisms built into sites of connection between components.

Figure 9H:
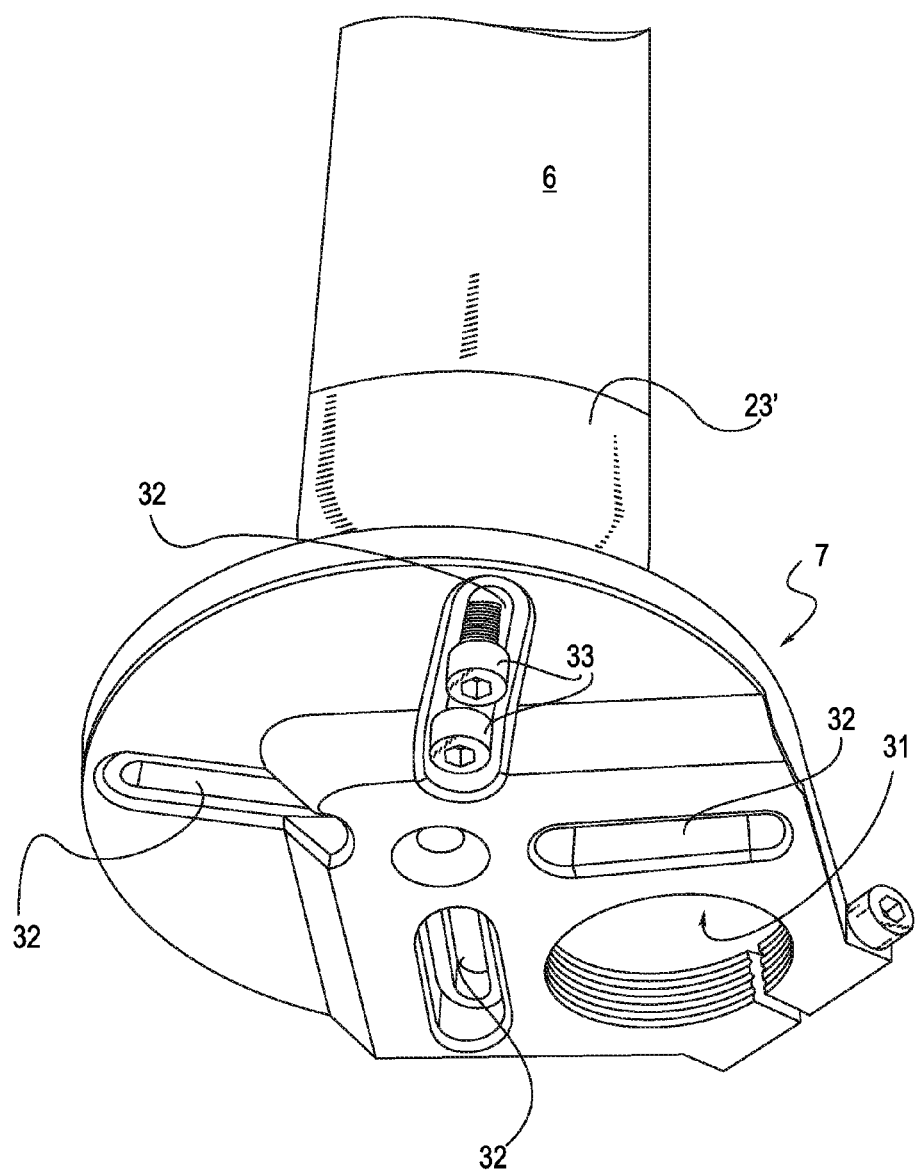
FIG. 9H is a lower perspective view of a distal base with a single strut connected thereto, showing connecting bolts inserted through a strut slot in the distal base, according to one embodiment.

FIG. 9H shows a lower perspective view of a distal base embodiment 7 with a single strut 6 connected thereto, and further showing connecting bolts 33 inserted through a strut slot 32 in the distal base. When these bolts 33 are loose, strut 6 is free to slide in and out radially to a desired position. When bolts 33 are tightened, strut 6 is securely locked at the desired position. By virtue of this variability in radial position of each strut 6 within a respective strut slot 32, the volume and shape of internal space within the prosthetic socket can be controlled. Further (not shown), struts 6 are pivotable when the bolts 33 are loose, and fixed in position when the bolts are tight. Accordingly, at least by virtue of modular distal bases 7 of variable shape and size, by virtue of modular struts 6 of variable size and shape, and by virtue of the degrees of freedom provided by the connectability of struts 6 and bases 7, a wide range of sizes and shapes of modular prosthetic sockets 100 are provided.

Figure 10A:
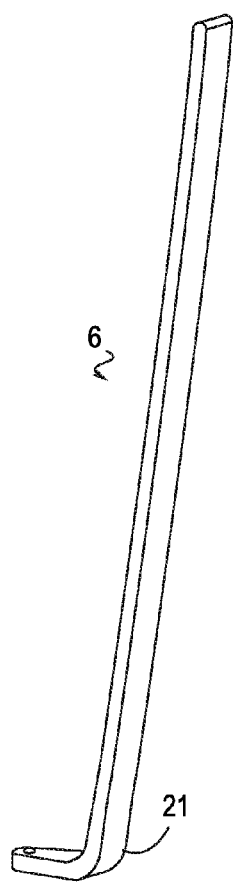
FIGS. 10A-10D are perspective views of a thermoplastic-fiber composite strut in an original configuration and in a thermally reformed configuration, according to one embodiment.

FIGS. 10A-10D show embodiments of a thermoplastic-fiber composite strut 6 in an initial state, as it was originally formed, and three examples of the strut after being thermally reformed to better fit against a portion of the residual limb. (Aspects of thermoplastic-fiber composition of the struts and thermal reforming methods of struts are described in detail in U.S. patent application Ser. No. 14/213,788.) FIG. 10A shows a strut 6 in a neutral or substantially flat configuration. These strut embodiments have been molded so as to have a contoured distal end 21, as described above. This configuration may be formed in the initial molding or applied secondarily in a thermal reforming step. Curved take off angle 24, itself, is a variable that is included among the modular variations of strut configuration.

Figure 10B:
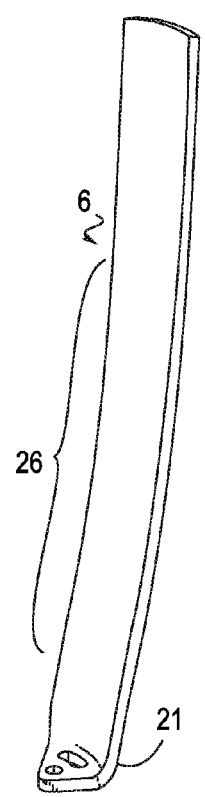
Figure 10C:
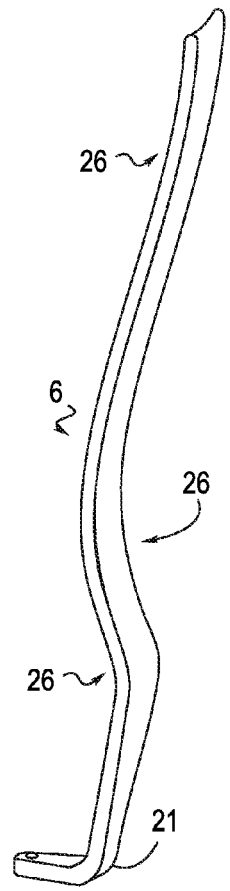
Figure 10D:
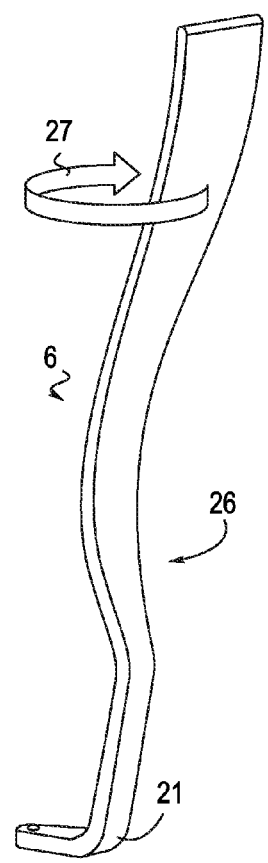
Figure 11:
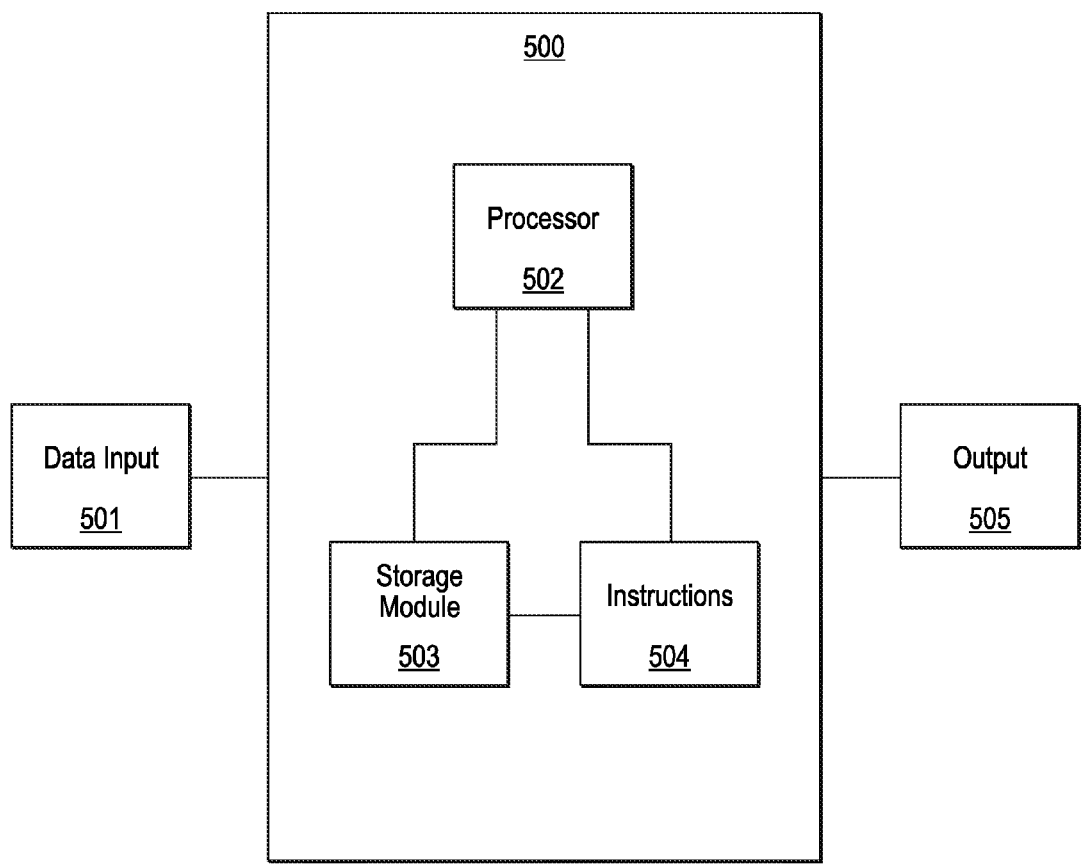
FIG. 11 is a block diagram illustrating a system for delivering mass customized modular prosthetic sockets, according to one embodiment.

The two-dimensional aspect of the shape of struts 6 in FIGS. 10A-10D is substantially flat and advantageous for allowing them to be cut from slat stock material (or requiring only a simple mold), and a good neutral starting shape that can be later reformed toward a desired shape for better fitting of a residual limb. FIG. 10A shows a strut in a neutral flat shape. FIG. 10B shows a strut 6 after it has been reformed to include a broadly distributed internally bowed curve 26. Contours 26 directed in either internally or externally may be imparted at any point along the length a strut, and more than one curve 26 may be included. Contours in the form of twists 27 may also be imparted by thermal reforming. Multiple curves 26 can be imparted in a reforming process at the same time, or they can be added serially. FIG. 10C shows a strut 6 with multiple reformed contours 26. FIG. 10D shows a strut 6 (similar to that of FIG. 10C) after the strut has been thermally reformed to include a twist 27 of several degrees. A twist 27, as imparted by a reforming process, may be advantageous for the fitting of modular prosthetic sockets to particular residual limbs.

The thermal reforming of struts 6 thus imparts an additional aspect of the modular character of this thermoplastic-fiber composite component that elaborates on the basic variations in dimensions of native or initially formed struts 6, as shown in FIGS. 9A-9E. Accordingly, by these modular dimensional variations, by thermal reforming, and by virtue of the connectability of struts 6 to distal base 7, a wide range of shapes and sizes of modular prosthetic socket 100 may be assembled.

FIG. 11 is a schematic diagram of a system 500 for the mass customization of modular prosthetic sockets 100 that may be provided to one or multiple patients, each patient receiving an individual-specific prosthetic socket 100. A description of mass customization and a recitation of technologies that underlie implementation of mass customization as directed to delivering a custom-fitted modular prosthetic socket to multiple patients is described above. Input 501 to system 500 includes a digital profile of each patient's residual limb, for which an individually assembled and configured modular prosthetic socket will be fabricated, as described in detail above.

The system includes a processor 501, a storage module 502, and instructions 503 that drive output 505 in the form of implementing method steps. Instruction 503 are put into the system in the form of rules and algorithms, as may be derived from component specifications, and from accumulated empirical data. Residual limb profile data input 501 is received (as conveyed from a clinical prosthetics facility) by system 500 and stored in the storage module 502 along with identifying attributes that allow retrieval so that instructions 504 can engage the individual residual limb profile and generate patient-specific output. Typically, output 505 relates to initiating methods of identifying or selecting appropriate prosthetic socket components, registering the profile data on a modular prosthetic socket template that includes all modular component specifications, thermally reforming selected components as may be needed, assembling components or packaging components as a kit, and directing any of the components, kits, or assembled sockets ultimately to be shipped back to the clinical prosthetics facility that provided data input 501.

Embodiments of the technology are directed toward methods of mass customization of prosthetic sockets 100 such methods being operable by a system 500 of mass customization, as provided and described above. Some aspects of the method are practiced at one or more fabrication sites 2 and some aspects of the method are practiced at a clinical prosthetic facility 1. Some aspects of the method may be practiced at both or either of the sites. The fabrication site(s) 2 and the clinical prosthetic facility 1 cooperate and are in communication with regard to ultimately delivering a complete modular prosthetic socket 100 to the patient. In some aspects, the method may be characterized in terms of the logistics of the flow of digital information, modular prosthetic components, prosthetic socket kits, and complete prosthetic sockets between the sites. In another aspect, the method may be characterized in terms of which activities related to profiling the residual limb, selecting components, thermally reforming components, and assembling the prosthetic socket occur at either the clinical prosthetic facility 1 or the fabrication facility 2.

In one mass customization method embodiment, a method of assembling a modular prosthetic socket 100 for a residual limb of a patient includes receiving transmitted digital data that provide a profile of the residual limb; and applying the data toward selecting assembleable prosthetic socket components from component groups for assembly into an intended prosthetic socket, the groups comprising (1) longitudinal struts 6 typically including a thermoplastic-fiber composite material; (2) proximal brim 8 members configured to be arranged proximal to the struts; and (3) distal socket bases 7 configured to be arranged distal to the struts. These selected assembleable components, collectively, are such that the intended modular prosthetic socket 100, when assembled therefrom, circumscribes or defines an internal space that is substantially complementary to profile of the residual limb. In typical embodiments of the method, at least one of the assembleable component groups comprises at least one of multiple sizes, shapes, or configurations of the respective assembleable component.

In some embodiments of the method, selecting assembleable components includes selecting from inventories of the groups of components. The method embodiment may further include assembling the selected assembleable components from inventories of components to yield the intended modular prosthetic socket 100. And in some embodiments, prior to the assembling step, the method may further include thermally reforming at least one of the selected components to improve a fit of the intended prosthetic socket to the residual limb of an individual patient. Embodiments of the method may further include, prior to an assembling step, shipping the selected assembleable components to a separate assembly site that is working cooperatively with the fabrication site 2.

Particular embodiments of the method may further include packaging the selected assembleable components from inventories of components to form a kit from which the intended modular prosthetic socket 100 may be assembled. Such method embodiment may further include sending the kit to a prosthetic clinical facility 1. At clinical facility 1, the method may further include assembling the kit components to yield the intended modular prosthetic socket. In some instances, a clinical facility 1 may assemble a prosthetic socket from components in an inventory. At clinical facility 1, the method may still further include, prior to the assembling step, thermally reforming at least one off the kit components so as to improve a fit of the intended prosthetic socket to the residual limb.

While some aspects of the method of assembling a modular prosthetic socket 100 for a residual limb of a patient may occur at a fabrication facility 2 that is equipped variously with fabrication equipment, thermal reforming equipment, warehouse space for inventory, and assembly space, some aspects of the method typically occur at clinical facility 1, where the patient is engaged by variously by prosthetists and technical staff or operators. At such a clinical site 1, embodiments of the method (prior to the step where the fabrication facility 2 receives digital data that profiles the residual limb) may include profiling the residual limb of the patient with regard to metrics of dimension and shape. Embodiments of this aspect of the method may further include rendering or processing the metrics of dimensions and shape into an operable or actionable digital profile applicable toward selecting assembleable prosthetic socket components from component groups based on the digital profile or directing a thermal reforming process. Processing the metrics of dimensions and shape may include shaping steps that modify the digital profile based on available templates, based on empirically derived algorithms, or based on input based on patient specific biomechanical considerations. In such embodiments, wherein the profiling and rendering steps are typically performed in a prosthetic clinical facility 1, the method may further include transmitting the digital profile of the residual limb, or an actionable derivative thereof, to a prosthetic socket fabrication facility 2.

As final steps in the delivery of a custom-fitted modular prosthetic socket 100 to a patient at a clinical prosthetic facility 1, a prosthetist makes mechanical adjustments of the socket, particularly the positioning of struts 6 on the distal base 7. Additionally, a prosthetist trains the patient how to make tension adjustments with the adjustable tensioning systems 45 and 46.

Returning now to embodiments of the method of assembling a modular prosthetic socket 100 as described above, and as practiced at one or more fabrication facilities 2, such methods may further include fabricating components from one or more, or each of the prosthetic socket component groups (i.e., struts 6, brim members 8, and distal bases 7), as well as other modular components, such as distal cup 9, by way of example. Embodiments of the method may further include stocking the fabricated components from each of the prosthetic socket component groups as component inventories. And method embodiments may further include shipping the fabricated components from each of the prosthetic socket component groups to a clinical prosthetic facility 1, there to be stocked as component inventories.

The scope of the technology disclosed herein and for which claims may be made, is such that any feature or method step shown or described in the context of a given embodiment or example may be included within or combined with any other embodiment or example shown or described. Further, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method of providing a modular prosthetic socket for a residual limb of a patient, the method comprising:
   receiving digital data defining a three-dimensional digital profile of the residual limb;
   selecting modular prosthetic socket components from component-specific inventories, based at least in part on the digital profile, the selected modular prosthetic socket components comprising:
      multiple longitudinal struts, wherein each strut comprises a proximal end, a distal end, and a thermoplastic-fiber composite material;
      one or more proximal brim members for attachment to the longitudinal struts at or near the proximal ends of the longitudinal struts; and
      a distal socket base to which the longitudinal struts attach at or near their distal ends; and
   providing the selected prosthetic components to an operator for assembling into the modular prosthetic socket, wherein the prosthetic socket, when assembled, includes at least three longitudinal struts and defines an internal space substantially complementary to the profile of the residual limb.

2. A method as in claim 1, wherein receiving the digital data comprises receiving the data at a fabrication facility from a clinical prosthetics facility.

3. A method as in claim 1, wherein at least one of the component-specific inventories comprises at least one of multiple sizes or shapes of the respective component.

4. A method as in claim 1, further comprising assembling the selected components together to yield the modular prosthetic socket.

5. A method as in claim 4, wherein assembling the selected components together comprises making adjustments to any of the components or to connections between the components that affect a configuration of the internal space defined by the prosthetic socket.

6. A method as in claim 1, further comprising, before the providing step, thermally reforming at least one of the longitudinal struts to improve a fit of the prosthetic socket to the residual limb.

7. A method as in claim 1, further comprising, before the providing step, packaging the selected components as a kit with instructions for use.

8. A method as in claim 7, further comprising sending the kit to a clinical prosthetics facility.

9. A method as in claim 1, further comprising, before the receiving step, profiling the residual limb of the patient with regard to metrics of dimension and shape to yield the digital profile.

10. A method as in claim 9, wherein profiling the residual limb comprises employing at least one technique selected from the group consisting of methods of manual measurements, tomography, magnetic resonance tomography, X-ray, ultrasound, radiofrequency, acoustic compliance, scanning, photography, photogrammetry, casting, and mapping with a three dimensional point reference device a three-dimensional digital and physical representation of the residual limb.

11. A method as in claim 9, further comprising rendering the digital profile to be operable for at least one of selecting the prosthetic socket components or thermally reforming the components.

12. A method as in claim 11, wherein the profiling and rendering steps are performed in a clinical prosthetics facility, the method further comprising transmitting the digital profile of the residual limb from the clinical prosthetics facility to a prosthetic socket fabrication facility.

13. A method as in claim 1, further comprising, before the selecting step, fabricating the components from at least one of the prosthetic socket component groups, based at least in part on the digital profile.

14. A method as in claim 1, wherein the providing step comprises shipping the selected components to a clinical prosthetics facility.

15. A method of providing modular prosthetic sockets for residual limbs of multiple patients, the method comprising:
   receiving digital data defining three-dimensional profiles of the residual limbs of the multiple patients;
   selecting modular prosthetic socket components from component-specific inventories for assembly of multiple modular prosthetic sockets, based at least in part on the digital profiles, the selected modular prosthetic socket components comprising:
      multiple longitudinal struts, wherein each strut comprises a proximal end, a distal end, and a thermoplastic-fiber composite material;
      one or more proximal brim members for attachment to the longitudinal struts at or near the proximal ends of the longitudinal struts; and
      a distal socket base to which the longitudinal struts attach at or near their distal ends; and providing the selected prosthetic components to at least one operator, wherein each of the modular prosthetic sockets, when assembled from the selected modular prosthetic socket components, includes at least three longitudinal struts and defines an internal space substantially complementary to the profile of the residual limb of one of the multiple patients.

16. A method as in claim 15, wherein receiving the digital data comprises receiving the data at a fabrication facility from a clinical prosthetics facility.

17. A method as in claim 15, wherein at least one of the component inventories comprises at least one of multiple sizes or shapes of the respective component.

18. A method as in claim 15, further comprising assembling the selected components together to yield the modular prosthetic sockets.

19. A method as in claim 18, wherein assembling the selected components together comprises making adjustments to any of the components or to connections between the components that affect a configuration of the internal space defined by any of the prosthetic sockets.

20. A method as in claim 15, further comprising, before the providing step, thermally reforming at least one of the longitudinal struts of one of the modular prosthetic sockets to improve a fit of one of the modular prosthetic sockets to the residual limb of one of the patients.

21. A method as in claim 15, further comprising, before the providing step, packaging the selected components as a kit with instructions for use.

22. A method as in claim 21, further comprising sending the kit to a clinical prosthetics facility.

23. A method as in claim 15, further comprising, before the receiving step, profiling the residual limb of the multiple patients with regard to metrics of dimension and shape to yield the digital profile of each of the multiple patients.

24. A method as in claim 23, wherein the profiling the residual limb comprises employing a method selected from the group consisting of manual measurements, tomography, magnetic resonance tomography, X-ray, ultrasound, radiofrequency, acoustic compliance, scanning, photography, photogrammetry, casting, and mapping with a three dimensional point reference device a three-dimensional digital and physical representation of the residual limb of each of the multiple patients.

25. A method as in claim 23, further comprising rendering the digital profiles to be operable for at least one of selecting the prosthetic socket components or thermally reforming the components.

26. A method as in claim 25, wherein the profiling and rendering steps are performed in one or more clinical prosthetics facilities, the method further comprising transmitting the digital profiles of the residual limbs from the clinical prosthetics facilities to one or more prosthetic socket fabrication facilities.

27. A method as in claim 15, further comprising, before the selecting step, fabricating components from at least one of the prosthetic socket component groups, based at least in part on the digital profiles.

28. A method as in claim 27, wherein the providing step comprises shipping the selected components to a clinical prosthetics facility.

29. A system for providing modular prosthetic sockets for residual limbs of multiple patients, the system comprising:
an inventory of modular prosthetic socket components for assembling multiple modular prosthetic sockets, the assembling based at least in part on a digital profile of the residual limb, the modular prosthetic socket components comprising;
multiple longitudinal struts, wherein each strut comprises a proximal, a distal end, and a thermoplastic-fiber composite material;
one or more proximal brim members for attachment to the longitudinal struts at or near the proximal ends of the longitudinal struts; and
a distal socket base to which the longitudinal struts attach at or near their distal ends; and
a data storage device storing instructions for selecting patient-specific prosthetic socket components from the inventory; and
a processor configured to execute the instructions to perform a method, the performed method comprising:
receiving digital data defining three-dimensional profiles of the residual limbs of the multiple patients; and
selecting the patient-specific prosthetic socket components from the inventory for assembly of multiple modular prosthetic sockets, based at least in part on the digital data,
wherein each of the modular prosthetic sockets, when assembled from the selected prosthetic components, includes at least three longitudinal struts and defines an internal space substantially complementary to the profiles of the residual limbs.

30. A system as in claim 29, wherein receiving the digital data comprises receiving the data at a fabrication facility from a clinical prosthetics facility.

31. A system as in claim 29, wherein at least one of the component inventories comprises at least one of multiple sizes or shapes of the respective component.

32. A system as in claim 29, wherein the method further comprises assembling the selected components together to yield the modular prosthetic sockets.

33. A system as in claim 32, wherein the assembling the selected components together comprises making adjustments to any of the components or to connections between the components that affect a configuration of the internal space defined by any of the prosthetic sockets.

34. A system as in claim 32, wherein the method, prior to the assembling step, further comprises thermally reforming at least one of the longitudinal struts of one of the modular prosthetic sockets to improve a fit of one of the modular prosthetic sockets to the residual limb of one of the patients.

35. A system as in claim 32, wherein the method, prior to the assembling step, further comprises packaging the selected components from inventories of components as a kit with instructions for use.

36. A system as in claim 35, wherein the method further comprises sending the kit to a clinical prosthetics facility.

37. A system as in claim 29, wherein the method, prior to the receiving step, further comprises profiling the residual limb of the multiple patients with regard to metrics of dimension and shape to yield the digital profile of the residual limb of each of the multiple patients.

38. A system as in claim 37, wherein profiling the residual limb comprises employing a method selected from the group consisting of manual measurements, tomography, magnetic resonance tomography, X-ray, ultrasound, radiofrequency, acoustic compliance, scanning, photography, photogrammetry, casting, and mapping with a three dimensional point reference device a three-dimensional digital and physical representation of the residual limb.

39. A system as in claim 37, wherein the method further comprises rendering the digital profiles to be operable for at least one of selecting prosthetic socket components or thermally reforming the components.

40. A system as in claim 39, wherein the profiling and rendering steps are performed in a clinical prosthetics facility, the method further comprising transmitting the digital profiles of the residual limbs from the clinical prosthetics facility to a prosthetic socket fabrication facility.

41. A system as in claim 29, wherein the method further comprises fabricating components from at least one of the prosthetic socket component groups, based at least in part on the digital profiles.

42. A system as in claim 29, wherein the method further comprises shipping the selected components to a clinical prosthetics facility.

* * * * *